US012767712B2

(12) United States Patent
Germinaro et al.

(10) Patent No.: US 12,767,712 B2
(45) Date of Patent: Oct. 20, 2026

(54) METHODS OF TREATING CROHN'S DISEASE WITH ANTI-IL23 SPECIFIC ANTIBODY

(71) Applicant: Janssen Biotech, Inc., Horsham, PA (US)

(72) Inventors: Matthew Germinaro, Philadelphia, PA (US); Mobolaji Olurinde, Lansdale, PA (US); Aparna Sahoo, Princeton, NJ (US); Jacqueline Yee, Raritan, NJ (US); Omoniyi Adedokun, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 373 days.

(21) Appl. No.: 17/974,956

(22) Filed: Oct. 27, 2022

(65) Prior Publication Data

US 2024/0141032 A1 May 2, 2024

Related U.S. Application Data

(60) Provisional application No. 63/273,239, filed on Oct. 29, 2021.

(51) Int. Cl.

| | |
|---|---|
| ***C07K 16/24*** | (2006.01) |
| ***A61P 37/02*** | (2006.01) |
| *A61K 39/00* | (2006.01) |

(52) U.S. Cl.

CPC ............ *C07K 16/244* (2013.01); *A61P 37/02* (2018.01); *A61K 2039/505* (2013.01); *A61K 2039/545* (2013.01); *C07K 2317/565* (2013.01)

(58) Field of Classification Search

CPC ............ C07K 16/244; C07K 2317/565; C07K 2317/21; A61P 37/02; A61K 2039/505; A61K 2039/545

See application file for complete search history.

(56) References Cited

U.S. PATENT DOCUMENTS

| | | | | |
|---|---|---|---|---|
| 5,750,373 | A | 5/1998 | Garrard et al. | |
| 5,859,205 | A | 1/1999 | Adair et al. | |
| 6,060,284 | A | 5/2000 | Bazan | |
| 6,479,634 | B1 | 11/2002 | Bazan | |
| 6,495,667 | B1 | 12/2002 | Bazan | |
| 6,610,285 | B1 | 8/2003 | Hirata | |
| 6,756,481 | B2 | 6/2004 | Chirica et al. | |
| 6,800,460 | B1 | 10/2004 | Oppmann et al. | |
| 6,835,825 | B1 | 12/2004 | Bazan | |
| RE39,015 | E | 3/2006 | Bazan | |
| 7,090,847 | B1 | 8/2006 | Oppmann et al. | |
| 7,183,382 | B2 | 2/2007 | Oppmann et al. | |
| 7,247,711 | B2 | 7/2007 | Benson et al. | |
| 7,252,971 | B2 | 8/2007 | Benson et al. | |
| 7,282,204 | B2 | 10/2007 | Oft et al. | |
| 7,491,391 | B2 | 2/2009 | Mark et al. | |
| 7,807,414 | B2 | 10/2010 | Mark et al. | |
| 7,935,344 | B2 * | 5/2011 | Benson | A61K 9/0019 424/145.1 |
| 7,993,645 | B2 | 8/2011 | Benson | |
| 8,106,177 | B2 | 1/2012 | Benson | |
| 8,221,760 | B2 | 7/2012 | Benson | |
| 9,353,181 | B2 | 5/2016 | Benson et al. | |
| 9,353,645 | B1 | 5/2016 | Kennedy | |
| 9,725,470 | B2 | 8/2017 | Hudson et al. | |
| 9,783,607 | B2 | 10/2017 | Benson | |
| 9,803,010 | B2 | 10/2017 | Reichert | |
| 10,030,070 | B2 | 7/2018 | Benson | |
| 10,072,026 | B2 | 9/2018 | Huang et al. | |
| 11,780,911 | B2 | 10/2023 | Germinaro et al. | |
| 12,138,295 | B2 * | 11/2024 | Adedokun | A61P 1/00 |
| 2002/0042386 | A1 | 4/2002 | Rosen et al. | |
| 2003/0124617 | A1 | 7/2003 | Gram et al. | |
| 2003/0162261 | A1 | 8/2003 | Oppmann et al. | |
| 2004/0185506 | A1 | 9/2004 | Heavner | |
| 2004/0258686 | A1 | 12/2004 | Chirica et al. | |
| 2005/0049402 | A1 | 3/2005 | Babcook et al. | |
| 2005/0053598 | A1 | 3/2005 | Burke et al. | |
| 2005/0175611 | A1 | 8/2005 | Mahler et al. | |
| 2005/0208052 | A1 | 9/2005 | Katsikis et al. | |
| 2005/0244874 | A1 | 11/2005 | Kastelein et al. | |
| 2007/0048315 | A1 | 3/2007 | Presta | |
| 2007/0218064 | A1 * | 9/2007 | Benson | C07K 16/244 536/23.53 |
| 2010/0322863 | A1 | 12/2010 | Benson et al. | |

(Continued)

FOREIGN PATENT DOCUMENTS

| | | |
|---|---|---|
| WO | 2007076524 A2 | 7/2007 |
| WO | 2014004436 A2 | 1/2014 |

(Continued)

OTHER PUBLICATIONS

Edwards, B. M. et al. The Remarkable Flexibility of the Human Antibody Repertoire; Isolation of Over One Thousand Different Antibodies to a Single Protein, BLyS. J Mol Biol 2003; 334:103-118. (Year: 2003).*

Goel, M. et al. Plasticity within the Antigen-Combining Site May Manifest as Molecular Mimicry in the Humoral Immune Response. J Immunol 2004; 173:7358-7367. (Year: 2004).*

Almagro, J.C. & Fransson, J. Humanization of Antibodies. Frontiers in Bioscience 2008; 13:1619-33. (Year: 2008).*

Lloyd, C. et al. Modelling the human immune response: performance of a 1011 human antibody repertoire against a broad panel of therapeutically relevant antigens. Protein Eng Des Sel 2009; 22;3:159-168. (Year: 2009).*

Wehkamp J. et al. Inflammatory Bowel Disease: Crohn's disease and ulcerative colitis. Dtsch Arztebl Int 2016, 113: 72-82. (Year: 2016).*

Briney, B. et al. Commonality despite exceptional diversity in the baseline human antibody repertoire. Nature 2019; 566: 393-397 (Year: 2019).*

(Continued)

*Primary Examiner* — Misook Yu
*Assistant Examiner* — Grace H Lunde

(57) ABSTRACT

A method of treating Crohn's disease in a patient by administering an IL-23 specific antibody, e.g., guselkumab, at an initial subcutaneous dose and subsequent subcutaneous doses in order for the patient to respond to the antibody and meet one or more of the clinical endpoints.

29 Claims, 2 Drawing Sheets

Specification includes a Sequence Listing.

(56) References Cited

U.S. PATENT DOCUMENTS

| | | | | |
|---|---|---|---|---|
| 2011/0287028 | A1 | 11/2011 | Benson | |
| 2011/0319292 | A1 | 12/2011 | Mark et al. | |
| 2014/0093203 | A1 | 4/2014 | Chen et al. | |
| 2015/0147337 | A1 | 5/2015 | Reichert et al. | |
| 2016/0237151 | A1 | 8/2016 | Benson | |
| 2017/0081402 | A1 | 3/2017 | Boecher | |
| 2017/0107266 | A1 | 4/2017 | Hinner et al. | |
| 2018/0036379 | A1 | 2/2018 | Chevrier et al. | |
| 2018/0094052 | A1 | 4/2018 | Randazzo | |
| 2018/0218215 | A1 | 8/2018 | Quenard et al. | |
| 2019/0246455 | A1 | 8/2019 | Weber et al. | |
| 2019/0269757 | A1* | 9/2019 | Adedokun | A61P 37/06 |
| 2020/0095315 | A1 | 3/2020 | Johans et al. | |
| 2021/0308220 | A1 | 10/2021 | Adedokun et al. | |
| 2022/0112219 | A1 | 4/2022 | Kraut et al. | |
| 2022/0112220 | A1 | 4/2022 | Nitert et al. | |
| 2023/0122171 | A1 | 4/2023 | Shiff et al. | |
| 2023/0151087 | A1 | 5/2023 | Adedokun et al. | |
| 2024/0199734 | A1 | 6/2024 | Germinaro et al. | |
| 2024/0368265 | A1 | 11/2024 | Adedokun et al. | |
| 2025/0090632 | A1 | 3/2025 | Adedokun et al. | |
| 2025/0129149 | A1 | 4/2025 | Fitzgerald et al. | |

FOREIGN PATENT DOCUMENTS

| | | | |
|---|---|---|---|
| WO | 2014093203 | A1 | 6/2014 |
| WO | 2015/119841 | A1 | 8/2015 |
| WO | 2017048901 | A1 | 3/2017 |
| WO | 2017049035 | A1 | 3/2017 |
| WO | 2017172771 | A2 | 10/2017 |
| WO | 2018218215 | A1 | 11/2018 |
| WO | 2019171252 | A1 | 9/2019 |
| WO | 2019246455 | A1 | 12/2019 |
| WO | 2020102519 | A1 | 5/2020 |

OTHER PUBLICATIONS

Ferrante M. et al. Risankizumab as maintenance therapy for moderately to severely active Crohn's disease: results from the multicentre, randomised, double-blind, placebo-controlled, withdrawal phase 3 FORTIFY maintenance trial. 2022 Lancet; 399, 10340: 2031-2046. (Year: 2022).*

Verstockt B. et al. IL-12 and IL-23 pathway inhibition in inflammatory bowel disease. 2023 Nat Rev Gastroenterol Hepatol; 20, 7: 433-446. (Year: 2023).*

STELARA, 112 pages, 2016.

"A study of the efficacy and safety of Guselkumab in participants with moderately to severely active crohn's disease (GALAXI)", Clinical Trial NCT03466411, Apr. 14, 2020, 6 Pages.

"U.S. FDA Approves Tremfya® (Guselkumab), the First and Only Il-23 Inhibitor Offering Both Subcutaneous and Intravenous Induction Options, for Adult Patients with Moderately to Severely Active Crohn's Disease", Innovative Medicine, Johnson & Johnson, 8 pages, Mar. 20, 2025.

Aggarwal et al., "Interleukin-23 promotes a distinct CD4 T cell activation state characterized by the production of interleukin-17", The Journal of Biological Chemistry, vol. 278, No. 3, pp. 1910-1914, 2003.

Barnes J Peter, "Cytokine-directed Therapies for the Treatment of Chronic Airway Diseases", Cytokine & Growth Factor Reviews 14, pp. 511-522, Dec 2003.

Barrie et al., "The Interleukin-12 Family of Cytokines: Therapeutic Targets for Inflammatory Disease Mediation", Clinical and Applied Immunology Reviews, vol. 5, pp. 225-240, 1995.

Belladonna et al., "Il-23 and Il-12 Have Overlapping, but Distinct, Effects on Murine Dendritic Cells", The Journal of Immunology, vol. 168, pp. 5448-5454, 2002.

Bhandari et al., "Discovery of Noval Oral Peptide Antagonists of IL-23 Receptor that are Efficacious in a Rat Model of IBD", Inflammatory Bowel Diseases, vol. 22, No. 1, pp. 148-148, Mar. 2016.

Boehringer, Ingelheim, "IL-23 Inhibitor Risankizumab Induces Remission in Phase II Study in Patients with Moderate-to-Severe Crohn's Disease", 04 pages, May 2016.

Centocor Ortho Biotech Inc., Retrieved from the Internet: URL: https://www.accessdata.fda.gov/drugsatfda_docs/label/2009/125261 s0011 b1 pdf on Jun. 13, 2019, pp. 1-12, Dec. 30, 2009.

Cohen et al., "Update on Anti-tumor Necrosis Factor Agents and Other New Drugs for Inflammatory Bowel Disease", BMJ, vol. 357, No. 2505, pp. 1-1, Jun. 19, 2019.

Cunningham et al., "High-resolution Epitope Mapping of Hgh-receptor Interactions by Alanine-scanning Mutagenesis", Science, vol. 244, No. 4908, pp. 1081-1085, Jun. 2, 1989.

D'Haens et al., "PP-0112 the Effect of Guselkumab Induction Therapy on Endoscopic Outcome Measures in Patients with Moderately to Severely Active Crohn's Disease: Week 12 Results from the Phase 2 GALAXI-1 Study", Journal of Gastroenterology and Hepatology, vol. 36, pp. 115, Aug. 1, 2021.

Danese et al., "Abstract Number: 1852, Clinical Efficacy and Safety of Guselkumab Maintenance Therapy in Patients with Moderately to Severely Active Crohn's Disease: week 48 analyses from the Phase 2 GALAXI 1 Study", Arthritis Rheumatol, vol. 74, No. 9, pp. 1-6, Nov. 14, 2022.

Danese et al., "OP28 The Effect of Guselkumab Induction Therapy on Early Clinical Outcome Measures in Patients with Moderately to Severely Active Crohn's Disease: Results from the Phase 2 GALAXI 1 Study", Journal of Crohn's and Colitis, vol. 15, No. 1, pp. S027-S028, May 27, 2021.

Davidson et al., "IL-12, But Not IFN-y, plays a Major Role in Sustaining the Chronic Phase of Colitis inIL-10-deficient mice", The Journal of Immunology, vol. 161, pp. 3143-3149, 1998.

Eduardo Padlan, "Anatomy of the Antibody Molecule," Molecular Immunology, vol. 31, No. 3, pp. 169-217, 1994.

Fan et al., "Mixed Treatment Comparison of Infliximab with Ustekinumab in Patients with Moderate to Severe Psoriasis,", British Journal of Dermatology, Abstract P-64, 2011.

Feagan et al., "Induction Therapy with the Selective Interleukin-23 Inhibitor Risankizumab in Patients with Moderate-to-Severe Crohn's Disease: A Randomised, Double-blind, Placebo-Controlled Phase 2 Study", The Lancet, vol. 389, pp. 1699-1709, Apr. 29, 2017.

Feagan et al., "Ustekinumab as Induction and Maintenance Therapy for Crohn's Disease", The New England Journal of Medicine, vol. 375, No. 20, pp. 1946-1960, Nov. 17, 2016.

Frucht M David, "Il-23: A Cytokine That Acts on Memory T Cells", Science STKE, vol. 114, pp. 1-3, Jan. 8, 2002.

Genaro, Alfonso R, "Remington's Pharmaceutical Sciences", Mack Publishing Company, Edition 17, Chapter 19, 16 pages, 1985.

Grolomoni et al., "The Role of IL-23 and the IL-23/TH17 Immune Axis in the Pathogenesis and Treatment of Psoriasis", Journal of the European Academy of Dermatology and Venereology, vol. 31, pp. 1616-1626, 2017.

Harlow et al., "Antibodies: A Laboratory Manual", Cold Spring Harbor Laboratory, Edition 2nd, 8 pages, 1989.

Hart et al., "Efficacy and Safety of Guselkumab Subcutaneous Induction and Maintenance in Participants with Moderately to Severely Active Crohn's Disease: Results from the Phase 3 GRAVITI Study", Gastroenterology, vol. 169, No. 2, pp. 308-325, Aug. 2025.

Hillier et al., GenBank Accession No. AA418747, 03 pages, May 12, 1997.

Hillier et al., GenBank Accession No. AA418955, 03 pages, May 12, 1997.

Hoffman, Alex, "Prefilled syringes point to the future,", Beremans Limited, pp. 1-4, 2004.

Hong et al., "IL-12, Independently of IFN-gamma, Plays a Crucial Role in the Pathogenesis of a Murine Psoriasis-like Skin Disorder", J Immunol., vol. 162, No. 12, pp. 7480-7491, Jun. 15, 1999.

Hu et al., "Information Contributed by Meta-analysis in Exposure-response Modeling: Application to Phase 2 Dose Selection of Guselkumab in Patients with Moderate-to-severe Psoriasis", Journal of Pharmacokinetics and Pharmacodynamics, vol. 41, No. 3, pp. 239-250, May 23, 2014.

International Search Report and Written Opinion received for PCT Application No. PCT/US2021/054004, mailed on Jan. 20, 2022, 11 pages.

(56) References Cited

OTHER PUBLICATIONS

International Search Report and Written Opinion received for PCT Application No. PCT/IB2021/053799, mailed on Jul. 27, 2021, 11 pages.
International Search Report and Written Opinion received for PCT Application No. PCT/IB2022/060353, mailed on Jan. 20, 2023, pp. 18.
Knappik et al., "Fully Synthetic Human Combinatorial Antibody Libraries (HuCAL) Based on Modular Consensus Frameworks and CDRs Randomized with Trinucleotides", Journal of Molecular Biology, vol. 296, pp. 57-86, 2000.
Kretzschmar et al., "Antibody Discovery: Phage Display", Current Opinion in Biotechnology, vol. 13, No. 6, pp. 598-602, Dec 2002.
Krnjevic-Pezic et al., "Our Experience Using Ustekinumab in Patients with Plaque Psoriasis", British Journal of Dermatology, vol. 165, No. 6, 24 pages, Dec 2011.
Langrish et al., "IL-23 Drives a Pathogenic T Cell Population that Induces Autoimmune Inflammation", The Journal of Experimental Medicine, vol. 201, No. 2, pp. 233-240, Jan. 17, 2005.
Lee et al., "Increased Expression of Interleukin 23 p19 and p40 in Lesional Skin of Patients with Psoriasis Vulgaris", Journal of Experimental Medicine, vol. 199, No. 1, pp. 125-130, Jan. 5, 2004.
Leonard et al., "Prevention of Experimental Autoimmune Encephalomyelitis by Antibodies Against Interleukin 12", Journal of Experimental Medicine, vol. 181, No. 1, pp. 381-386, Jan. 1, 1995.
Macaluso et al., "Anti-interleukin-12 and Antiinterleukin-23 Agents in Crohn's Disease", Expert Opinion on Biological Therapy, vol. 19, No. 2, pp. 89-98, Dec 2018.
Malfait et al., "Blockade of IL-12 during the induction of collagen-induced arthritis (CIA) markedly attenuates the of the arthritis," Clinical and Experimental Immunology, vol. 111, pp. 327-383, 1998.
Megna et al., "Guselkumab for the Treatment of Psoriasis", Expert Opinion on Biological Therapy, vol. 18, No. 4, pp. 459-468, 2018.
Murphy et al., "Divergent Pro- and Anti-inflammatory Roles for Il-23 and Il-12 in Joint Autoimmune Inflammation", Journal of Experimental Medicine, vol. 198, No. 12, pp. 1951-1957, Dec 15, 2003.
Oppmann et al., "Novel p19 Protein Engages IL-12p40 to Form a Cytokine, IL-23, with Biological Activities Similar as Well as Distinct from IL-12", Immunity, vol. 13, No. 5, pp. 715-725, Nov. 1, 2000.
Oppmann et al., GenBank Accession No. AF301620, Dec. 4, 2000, 2 pages.
Panaccione et al., "Briakinumab for Treatment of Crohn's Disease: Results of a Randomized Trial", Inflamm Bowel Disease, vol. 21, No. 6, pp. 1329-1340, 2015.
Parham et al., "A Receptor for the Heterodimeric Cytokine Il-23 is Composed of IL-12R1 and a Novel Cytokine Receptor Subunit, IL-23R", The Journal of Immunology, vol. 168, No. 11, pp. 5699-5708, Dec 25, 2002.
Portolano et al., "Lack of Promiscuity in Autoantigen-specific H and L Chain Combinations as Revealed by Human H and L Chain Roulette", Journal of Immunology, vol. 150, No. 3, pp. 880-887, Feb. 1, 1993.
Presky et al., "A Functional Interleukin 12 Receptor Complex is Composed of two Beta-type Cytokine Receptor Subunits", Proceedings of the National Academy of Sciences of the United States of America, vol. 93, No. 24, pp. 14002-14007, Nov. 26, 1996.
Ramos et al., "Targeting Specific Immunologic Pathways in Crohn's Disease", Gastroenterol Clin N Am, vol. 46, No. 3, pp. 577-588, 2017.
Sandborn et al., "Guselkumab for the Treatment of Crohn's Disease: Induction Results from the Phase 2 GALAXI-1 Study", Gastroenterology, vol. 162, No. 6, pp. 1650-1664, May 1, 2022.
Sands et al., "PP-0132 the Effect of Guselkumab Induction Therapy on inflammatory Biomarkers in Patients with Moderately-to-severely Active Crohn's Disease: Week 12 Results from the Phase 2 GALAXI-1 Study", Journal of Gastroenterology and Hepatology, vol. 36, pp. 124-124, Aug. 1, 2021.
Schmidt et al., "Expression of Interleukin-12-related Cytokine Transcripts in Inflammatory Bowel Disease: Elevated Interleukin-23p19 and Interleukin-27p28 in Crohn's Disease but Not in Ulcerative Colitis", Inflamm Bowel Dis ., vol. 11, No. 1, pp. 16-23, Jan. 2005.
Seventer et al., "Interferon-β Differentially Regulates Expression of the Il-12 Family Members p35, p40, p19 and EB13 in Activated Human Dendritic Cells", Journal of Neuroimmunology, vol. 133, No. 1-2, pp. 60-71, Dec 2002.
Shi et al., "The state of the art on treatment of Crohn's disease", The Japanese Society of Gastroenterology, vol. 53, pp. 989-998, 2018.
Sofen et al., "Guselkumab (an Il-23-specific Mab) Demonstrates Clinical and Molecular Response in Patients with Moderate-to-severe Psoriasis", Journal of Allergy and Clinical Immunology, vol. 133, No. 4, pp. 1032-1040, Apr. 1, 2014.
Sofen et al., "Results of a Single Ascending Dose Study to Assess the Safety and Tolerability of Cnto1959 Following Intravenous or Subcutaneous Administration in Healthy Subjects and in Subjects with Moderate to Severe Psoriasis", British Journal of Dermatology, Abstract FC-21, 2011.
Takeda, J., GenBank Accession No. C06368, 02 pages, Aug. 9, 1996.
Trinchieri et al., "The IL-12 Family of Heterodimeric Cytokines: New Players in the Regulation of T Cell Responses", Immunity, vol. 19, No. 5, pp. 641-644, Nov. 2003.
Vajdos et al., "Comprehensive Functional Maps of the Antigen-binding Site of an Anti-ErbB2 Antibody Obtained with Shotgun Scanning Mutagenesis", J. Mol. Biol., vol. 320, No. 02, Jul. 5, 2002, pp. 415-428.
Visvanathan et al., "OP103 Selective IL-23 Inhibition by Risankizumab Modulates the Molecular Profile in the Colon of active Crohn's Disease Patients.", United European Gastroenterology Journal, vol. 4 (5S) A1-A156), pp. 1-3, Oct. 2016.
Wiekowski et al., "Ubiquitous Transgenic Expression of the Il-23 Subunit P19 Induces Multiorgan Inflammation, Runting, Infertility, and Premature Death", Journal of Immunology, vol. 166, No. 12, pp. 7563-7570, Jun. 15, 2001.
Wiendl et al., "Therapeutic Approaches in Multiple Sclerosis: Lessons from Failed and Interrupted Treatment Trials", BioDrugs, vol. 16, No. 3, pp. 183-200, 2002.
Yadav et al., "Cytokines and Autoimmunity: Redundancy Defines Their Complex Nature", Current Opinion in Immunology, vol. 15, No. 6, pp. 697-703, Dec 2003.
"Annex I—Summary of Product Characteristics", European Medicines Agency, XP055360688, pp. 1-112, Feb. 9, 2009.

* cited by examiner

METHODS OF TREATING CROHN'S DISEASE WITH ANTI-IL23 SPECIFIC ANTIBODY

CROSS-REFERENCE TO RELATED APPLICATIONS

This application claims the benefit of U.S. Provisional Application Ser. No. 63/273,239, filed 29 Oct. 2021. The entire contents of the aforementioned application are incorporated herein by reference in their entireties.

REFERENCE TO SEQUENCE LISTING SUBMITTED ELECTRONICALLY

This application contains a sequence listing, which is submitted electronically via The United States Patent and Trademark Center Patent Center as an XML formatted sequence listing with a file name "17974956_2_1.xml" and a creation date of Jul. 11, 2025, and having a size of 10,568 bytes. The sequence listing submitted via Patent Center is part of the specification and is herein incorporated by reference in its entirety.

FIELD OF THE INVENTION

The present invention is directed to methods of treating Crohn's Disease with an antibody that binds human IL23. In particular, it relates to dosing regimens for administration of an anti-IL23 specific antibody and specific pharmaceutical compositions of an antibody.

BACKGROUND OF THE INVENTION

Interleukin (IL)-12 is a secreted heterodimeric cytokine comprised of 2 disulfide-linked glycosylated protein subunits, designated p35 and p40 for their approximate molecular weights. IL-12 is produced primarily by antigen-presenting cells and drives cell-mediated immunity by binding to a two-chain receptor complex that is expressed on the surface of T cells or natural killer (NK) cells. The IL-12 receptor beta-1 (IL-12Rβ1) chain binds to the p40 subunit of IL-12, providing the primary interaction between IL-12 and its receptor. However, it is IL-12p35 ligation of the second receptor chain, IL-12Rβ2, that confers intracellular signaling (e.g., STAT4 phosphorylation) and activation of the receptor-bearing cell (Presky et al, 1996). IL-12 signaling concurrent with antigen presentation is thought to invoke T cell differentiation towards the T helper 1 (Th1) phenotype, characterized by interferon gamma (IFNγ) production (Trinchieri, 2003). Th1 cells are believed to promote immunity to some intracellular pathogens, generate complement-fixing antibody isotypes, and contribute to tumor immunosurveillance. Thus, IL-12 is thought to be a significant component to host defense immune mechanisms.

It was discovered that the p40 protein subunit of IL-12 can also associate with a separate protein subunit, designated p19, to form a novel cytokine, IL-23 (Oppman et al, 2000). IL-23 also signals through a two-chain receptor complex. Since the p40 subunit is shared between IL-12 and IL-23, it follows that the IL-12Rβ1 chain is also shared between IL-12 and IL-23. However, it is the IL-23p19 ligation of the second component of the IL-23 receptor complex, IL-23R, that confers IL-23 specific intracellular signaling (e.g., STAT3 phosphorylation) and subsequent IL-17 production by T cells (Parham et al, 2002; Aggarwal et al. 2003). Recent studies have demonstrated that the biological functions of IL-23 are distinct from those of IL-12, despite the structural similarity between the two cytokines (Langrish et al, 2005).

Abnormal regulation of IL-12 and Th1 cell populations has been associated with many immune-mediated diseases since neutralization of IL-12 by antibodies is effective in treating animal models of psoriasis, multiple sclerosis (MS), rheumatoid arthritis, inflammatory bowel disease, insulin-dependent (type 1) diabetes mellitus, and uveitis (Leonard et al, 1995; Hong et al, 1999; Malfait et al, 1998; Davidson et al, 1998). However, since these studies targeted the shared p40 subunit, both IL-12 and IL-23 were neutralized in vivo. Therefore, it was unclear whether IL-12 or IL-23 was mediating disease, or if both cytokines needed to be inhibited to achieve disease suppression. Recent studies have confirmed through IL-23p19 deficient mice or specific antibody neutralization of IL-23 that IL-23 inhibition can provide equivalent benefit as anti-IL-12p40 strategies (Cua et al, 2003, Murphy et al, 2003, Benson et al 2004). Therefore, there is increasing evidence for the specific role of IL-23 in immune-mediated disease. Neutralization of IL-23 without inhibition of IL-12 pathways could then provide effective therapy of immune-mediated disease with limited impact on important host defense immune mechanism. This would represent a significant improvement over other therapeutic options.

Currently, there are three classes of biologic agents approved for the treatment of moderately to severely active Crohn's disease: tumor necrosis factor (TNF) antagonist therapies (infliximab, adalimumab, certolizumab), integrin inhibitors (natalizumab and vedolizumab), and an IL-12/23 inhibitor (ustekinumab). Although the introduction of biologic agents has significantly improved the clinical management of patients with moderately to severely active Crohn's disease, a sizable proportion of the target patient population is non-responsive or will lose response over time. A review of the available data for approved biologic agents highlighted the unmet need in achieving and maintaining long-term remission, especially among patients who have previously failed biologic treatments. In all-treated patients (i.e., all patients who were randomized at Week 0 of the studies evaluated), the estimated rates of clinical remission at 1 year in the biologic failure or intolerance (BIO-Failure) population is around 20%, and ranges from 20% to 50% in the conventional therapy failure or intolerance (CON-Failure) population.

In summary, there remains considerable unmet medical need for new treatment options, especially therapies with novel mechanisms of action that have the potential to raise the efficacy bar and maximize the proportion of patients who achieve and maintain clinical remission.

SUMMARY OF THE INVENTION

In a first aspect, the invention concerns a method of treating a subject suffering from Crohn's disease comprising administering an anti-IL23 specific antibody (also referred to as IL23p19 or IL23p19 subunit antibody), e.g., guselkumab, to the patient in an initial subcutaneous induction dose from the start of treatment until 4 weeks from the start of treatment, and then subcutaneously administering the anti-IL-23 specific antibody once every 4 or 8 weeks thereafter, e.g., a dose at 0, 4, 8, 12 or 16, 20 or 24, 28 or 32, 36 or 40, 44 or 48 weeks. In addition, in another embodiment the subcutaneous treatment continues through 96 weeks or longer after the start of treatment.

In one embodiment, the subject receives the anti-IL23 specific antibody at a dose of 400 mg subcutaneously initially, 4 weeks after the initial dose and 8 weeks after the initial dose and continues with subcutaneous treatment of the anti-IL23 specific antibody at a dose of 100 mg or 200 mg every 4 weeks or every 8 weeks through 24 weeks after initial treatment and possibly continuing beyond 24 weeks through 48 weeks, 96 weeks and beyond.

In another aspect, the composition used in the method of the invention comprises a pharmaceutical composition comprising: an anti-IL23 specific antibody. In a preferred embodiment, the anti-IL-23 specific antibody is guselkumab in a composition of 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

In one embodiment, the anti-IL23 specific antibody will be provided at 200 mg/ml formulation in a single-dose prefilled syringe with YpsoMate autoinjector (PFS-Y) and in an alternative embodiment the anti-IL23 specific antibody will be provided at 100 mg/mL in a single-dose prefilled syringe with an UltraSafe Plus™ Passive Needle Guard (PFS-U).

In an embodiment, Crohn's disease patients achieve significant improvement in clinical endpoints selected from:

(i) Change from Baseline in the Crohn's Disease Activity Index (CDAI) Score; the CDAI score will be assessed by collecting information on 8 different Crohn's disease-related variables, with scores ranging from 0 to approximately 600. A decrease over time indicates improvement in disease activity;
(ii) Patient-Reported Outcome (PRO)-2 defined by the unweighted CDAI components of the total number of liquid or very soft stools and the abdominal pain (AP) score;
(iii) Endoscopic assessments of the intestinal mucosa based on the presence or absence of mucosal ulcerations and the Simple Endoscopic Score for Crohn's Disease (SES-CD);
(iv) Histologic assessments;
(v) Inflammatory pharmacodynamic (PD) markers including C-reactive protein (CRP) or fecal calprotectin;
(vi) Fistula assessment;
(vii) PRO measures to assess health-related quality of life outcomes including Inflammatory Bowel Disease Questionnaire (IBDQ) and Patient-reported Outcomes Measurement Information System (PROMIS)-29;
(viii) Patient-reported symptom measures including Bristol Stool Form Scale (BSFS) and AP-Numerical Rating Scale (NRS);
(ix) Clinical remission at Week 12, defined as CDAI less than (<) 150 points.
(x) Clinical response at Week 12, defined as greater than or equal to (>=) 100-point reduction from baseline in CDAI score or CDAI score <150.
(xi) Endoscopic Response at Week 12 measured by the Simple Endoscopic Score for Crohn's Disease (SES-CD). The SES-CD is based on the evaluation of 4 endoscopic components across 5 ileocolonic segments, with a total score ranging from 0 to 56.
(xii) Endoscopic Remission at Week 12 measured by the Simple Endoscopic Score for Crohn's Disease (SES-CD); SES-CD≤2.
(xiii) Clinical remission at Week 48 defined as CDAI score <150.
(xiv) Durable Clinical Remission at Week 48 defined as CDAI<150 for most of all visits between Week 12 and Week 48.
(xv) Corticosteroid-Free Clinical Remission at Week 48 defined as CDAI score <150 at Week 48 and not receiving corticosteroids at Week 48.
(xvi) PRO-2 remission at Week 48 defined based on average daily stool frequency (SF) and average daily abdominal pain (AP) score. Fatigue response at Week 12 based on the Patient-Reported Outcomes Measurement Information System (PROMIS). Fatigue Short Form 7a contains 7 items that evaluate the severity of fatigue, with higher scores indicating greater fatigue.

In another aspect of the invention the pharmaceutical composition comprises an isolated anti-IL23 specific antibody having the CDR sequences comprising (i) the heavy chain CDR amino acid sequences of SEQ ID NO: 1, SEQ ID NO: 2, and SEQ ID NO: 3; and (ii) the light chain CDR amino acid sequences of SEQ ID NO: 4, SEQ ID NO: 5, and SEQ ID NO: 6, optionally in a composition of 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

Another aspect of the method of the invention comprises administering a pharmaceutical composition comprising an isolated anti-IL-23 specific antibody having the heavy chain variable region amino acid sequence of SEQ ID NO: 7 and the light chain variable region amino acid sequence of SEQ ID NO: 8, optionally in a composition of 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

A further aspect of the method of the invention comprises administering a pharmaceutical composition comprising an isolated anti-IL-23 specific antibody having the heavy chain amino acid sequence of SEQ ID NO: 9 and the light chain amino acid sequence of SEQ ID NO: 10, optionally in a composition of 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

In a still further embodiment, the method of the invention comprises administering a pharmaceutical composition comprising the antibody guselkumab (marketed by Janssen Biotech, Inc as Tremfya®), optionally in a composition of 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

The details of one or more embodiments of the invention are set forth in the description below. Other features and advantages will be apparent from the following detailed description, figures, and the appended claims.

DETAILED DESCRIPTION OF THE PREFERRED EMBODIMENTS

Figure 1:
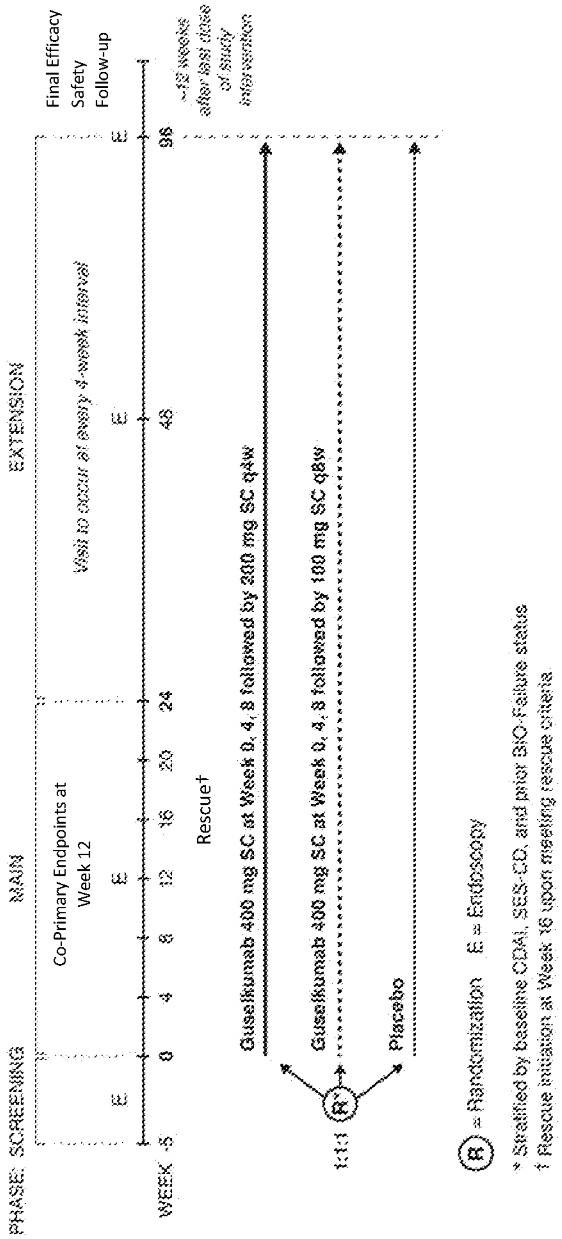
FIG. 1 shows a schematic overview of the study described herein.
Figure 2:
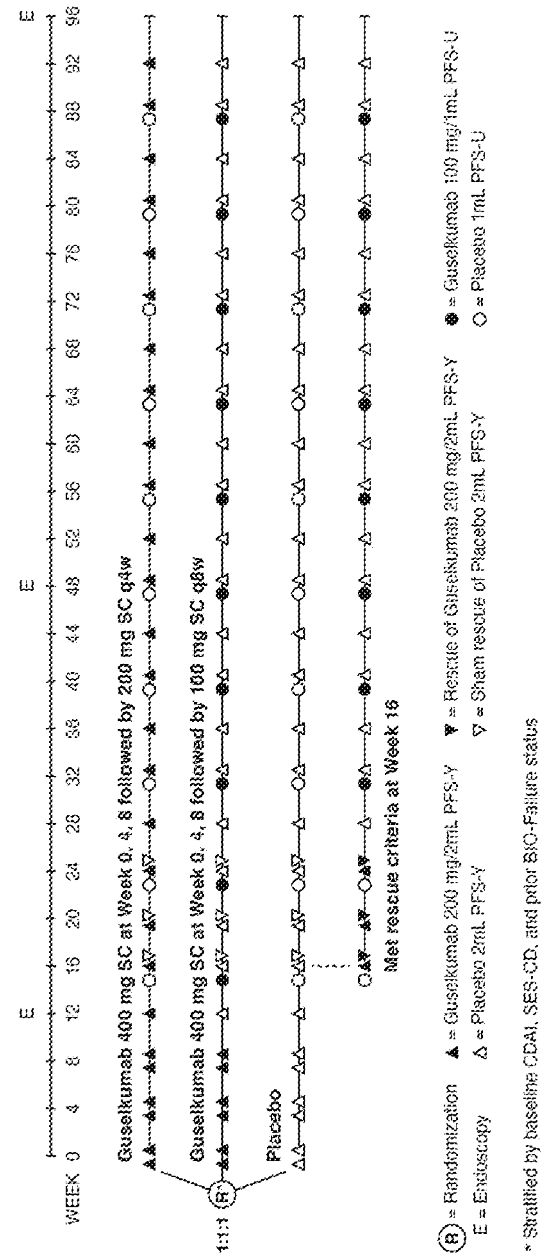
FIG. 2 shows the dosing regimens for the treatment phases and how study intervention will be administered.

As used herein the method of treatment of a subject suffering from Crohn's disease comprises administering isolated, recombinant and/or synthetic anti-IL-23 specific human antibodies and diagnostic and therapeutic compositions, methods and devices.

As used herein, an "anti-IL-23 specific antibody," "anti-IL-23 antibody," "antibody portion," or "antibody fragment" and/or "antibody variant" and the like include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an IL-23 receptor or binding protein, which can be incorporated into an antibody of the present invention. Such antibody optionally further affects a specific ligand, such as but not limited to, where such antibody modulates, decreases, increases, antagonizes, agonizes, mitigates, alleviates, blocks, inhibits, abrogates and/or interferes with at least one IL-23 activity or binding, or with IL-23 receptor activity or binding, in vitro, in situ and/or in vivo. As a non-limiting example, a suitable anti-IL-23 antibody, specified portion or variant of the present invention can bind at least one IL-23 molecule, or specified portions, variants or domains thereof. A suitable anti-IL-23 antibody, specified portion, or variant can also optionally affect at least one of IL-23 activity or function, such as but not limited to, RNA, DNA or protein synthesis, IL-23 release, IL-23 receptor signaling, membrane IL-23 cleavage, IL-23 activity, IL-23 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian IL-23. For example, antibody fragments capable of binding to IL-23 or portions thereof, including, but not limited to, Fab (e.g., by papain digestion), Fab' (e.g., by pepsin digestion and partial reduction) and $F(ab')_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a $F(ab')_2$ heavy chain portion can be designed to include DNA sequences encoding the $C_H1$ domain and/or hinge region of the heavy chain. The various portions of antibodies can be joined together chemically by conventional techniques or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A "human antibody" may also be an antibody that is derived from or closely matches human germline immunoglobulin sequences. Human antibodies may include amino acid residues not encoded by germline immunoglobulin sequences (e.g., mutations introduced by random or site-specific mutagenesis in vitro or by somatic mutation in vivo). Often, this means that the human antibody is substantially non-immunogenic in humans. Human antibodies have been classified into groupings based on their amino acid sequence similarities. Accordingly, using a sequence similarity search, an antibody with a similar linear sequence can be chosen as a template to create a human antibody. Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody.

It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably, human or humanized, antibodies that have binding specificities for at least two different antigens. In the present case, one of the binding specificities is for at least one IL-23 protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Anti-IL-23 specific (also termed IL-23 specific antibodies) (or antibodies to IL-23) useful in the methods and compositions of the present invention can optionally be characterized by high affinity binding to IL-23 and, optionally and preferably, having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titers in the patient treated (less than about 300, preferably less than about 100 measured with a double antigen enzyme immunoassay) (Elliott et al., *Lancet* 344: 1125-1127 (1994), entirely incorporated herein by reference). "Low immunogenicity" can also be defined as the incidence of titratable levels of antibodies to the anti-IL-23 antibody in patients treated with anti-IL-23 antibody as occurring in less than 25% of patients treated, preferably, in less than 10% of patients treated with the recommended dose for the recommended course of therapy during the treatment period.

The term "safe," as it relates to a dose, dosage regimen, treatment or method with an anti-IL-23 antibody of the present invention (e.g., the anti-IL-23 antibody guselkumab), refers to a relatively low or reduced frequency and/or low or reduced severity of treatment-emergent adverse events (referred to as AEs or TEAEs) from the clinical trials conducted, e.g., Phase 2 clinical trials and earlier, compared to the standard of care or to another comparator. An adverse event is an untoward medical occurrence in a patient administered a medicinal product. In particular, safe as it relates to a dose, dosage regimen or treatment with an anti-IL-23 antibody of the present invention refers to a relatively low or reduced frequency and/or low or reduced severity of adverse events associated with administration of the antibody if attribution is considered to be possible, probable, or very likely due to the use of the anti-IL-23 antibody.

Utility

The isolated nucleic acids of the present invention can be used for production of at least one anti-IL-23 antibody or specified variant thereof, which can be used to measure or effect in a cell, tissue, organ or animal (including mammals and humans), to diagnose, monitor, modulate, treat, alleviate, help prevent the incidence of, or reduce the symptoms of Crohn's disease.

Such a method can comprise administering an effective amount of a composition or a pharmaceutical composition comprising at least one anti-IL-23 antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts.

CITATIONS

All publications or patents cited herein, whether or not specifically designated, are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, NY (1987-2001); Sambrook, et al., Molecular Cloning: A Laboratory Manual, 2nd Edition, Cold Spring Harbor, NY (1989); Harlow and Lane, antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

Antibodies of the Present Invention-Production and Generation

At least one anti-IL-23 antibody used in the method of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, 2nd Edition, Cold Spring Harbor, NY (1989); Harlow and Lane, antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001), each entirely incorporated herein by reference.

A preferred anti-IL-23 antibody is guselkumab (also referred to as CNTO1959) having the heavy chain variable region amino acid sequence of SEQ ID NO: 7 and the light chain variable region amino acid sequence of SEQ ID NO: 8 and having the heavy chain CDR amino acid sequences of SEQ ID NO: 1, SEQ ID NO: 2, and SEQ ID NO: 3; and the light chain CDR amino acid sequences of SEQ ID NO: 4, SEQ ID NO: 5, and SEQ ID NO: 6. Other anti-IL-23 antibodies have sequences listed herein and are described in U.S. Pat. No. 7,935,344, the entire contents of which are incorporated herein by reference).

Human antibodies that are specific for human IL-23 proteins or fragments thereof can be raised against an appropriate immunogenic antigen, such as an isolated IL-23 protein and/or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, L243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like, or heteromylomas, fusion products thereof, or any cell or fusion cell derived therefrom, or any other suitable cell line as known in the art) (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; BioInvent, Lund, Sweden; Dyax Corp., Enzon, Affymax/Biosite; Xoma, Berkeley, CA; Ixsys. Sec, e.g., EP 368,684, PCT/GB91/01134; PCT/GB92/01755; PCT/GB92/002240; PCT/GB92/00883; PCT/GB93/00605; U.S. Ser. No. 08/350,260 (5/12/94); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); WO96/13583, WO97/08320 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins-U.S. Pat. Nos. 5,723,323, 5,763,192, 5,814,476, 5,817,483, 5,824,514, 5,976,862, WO 86/05803, EP 590 689 (Ixsys, predecessor of Applied Molecular Evolution (AME), each entirely incorporated herein by reference)) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, MA; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is non-human, e.g., but not limited to, mouse, rat, rabbit, non-human primate or other mammal. These non-human amino acid residues are replaced by residues often referred to as "import" residues, which are typically taken from an "import" variable, constant or other domain of a known human sequence.

Known human Ig sequences are disclosed, e.g., www.ncbi.nlm.nih.gov/entrez/query.fcgi; www.ncbi.nih.gov/igblast; www.atcc.org/phage/hdb.html; www.mrc-cpc.cam.ac.uk/ALIGNMENTS.php; www.kabatdatabase.com/top.html; ftp.ncbi.nih.gov/repository/kabat; www.sci-quest.com; www.abcam.com; www.antibodyresource.com/onlinecomp.html; www.public.iastate.edu/~pedro/research_tools.html; www.whfreeman.com/immunology/CH05/kuby05.htm; www.hhmi.org/grants/lectures/1996/vlab; www.path.cam.ac.uk/~mrc7/mikeimages.html; mcb.harvard.edu/BioLinks/Immunology.html; www.immunologylink.com; pathbox.wustl.cdu/~hcenter/index.html; www.appliedbiosystems.com; www.nal.usda.gov/awic/pubs/antibody; www.m.chime-u.ac.jp/~yasuhito/Elisa.html; www.biodesign.com; www.cancerresearchuk.org; www.biotech.ufl.edu; www.isac-net.org; baserv.uci.kun.nl/~jraats/links1.html; www.recab.uni-hd.de/immuno.bme.nwu.edu; www.mrc-cpc.cam.ac.uk; www.ibt.unam.mx/vir/V_mice.html; www.bioinf.org.uk/abs; antibody.bath.ac.uk; www.unizh.ch; www.cryst.bbk.ac.uk/~ubcg07s; www.nimr.mrc.ac.uk/CC/ccacwg/ccacwg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antigen binding. Accordingly, part or all of the non-human or human CDR sequences are maintained while the non-human sequences of the variable and constant regions may be replaced with human or other amino acids.

Antibodies can also optionally be humanized or human antibodies engineered with retention of high affinity for the antigen and other favorable biological properties. To achieve this goal, humanized (or human) antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

In addition, the human IL-23 specific antibody used in the method of the present invention may comprise a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6.

In other embodiments, the human IL-23 specific antibody used in the method of the present invention may comprise a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework (readily available at the sources of known human Ig sequences described above). In other embodiments, at least FRH1, FRH2, FRH3, or FRH4 is a germline sequence (e.g., human germline) or comprises human consensus sequences for the particular framework. In preferred embodiments, the framework region is a fully human framework region.

Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151:2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766886, 5714352, 6204023, 6180370, 5693762, 5530101, 5585089, 5225539; 4816567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype. Alternatively or additionally, it may be useful to combine amino acid modifications with one or more further amino acid modifications that alter C1q binding and/or the complement dependent cytotoxicity function of the Fc region of an IL-23 binding molecule. The starting polypeptide of particular interest may be one that binds to C1q and displays complement dependent cytotoxicity (CDC). Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO0042072, which is hereby incorporated by reference.

As disclosed above, one can design an Fc region of the human IL-23 specific antibody of the present invention with altered effector function, e.g., by modifying C1q binding and/or FcγR binding and thereby changing complement dependent cytotoxicity (CDC) activity and/or antibody-dependent cell-mediated cytotoxicity (ADCC) activity. "Effector functions" are responsible for activating or diminishing a biological activity (e.g., in a subject). Examples of effector functions include, but are not limited to: C1q binding; CDC; Fc receptor binding; ADCC; phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the human IL-23 (or anti-IL-23) antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

Fc mutations can also be introduced in engineer to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, J. Biol. Chem. 276:6591-6604).

Another type of amino acid substitution serves to alter the glycosylation pattern of the Fc region of the human IL-23 specific antibody. Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation sites that are not present in the polypeptide. Addition of glycosylation sites to the Fc region of a human IL-23 specific antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the human IL-23 specific antibody of the present invention is expressed in cells that express beta (1,4)—N-acetylglucosaminyltransferase III (GnT III), such that GnT III adds GlcNAc to the human IL-23 antibody. Methods for producing antibodies in such a fashion are provided in WO/9954342, WO/03011878, patent publication 20030003097A1, and Umana et al., Nature Biotechnology, 17:176-180, February 1999; all of which are herein specifically incorporated by reference in their entireties.

The anti-IL-23 antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-IL-23 antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. *Nature* 368:856-859 (1994), Taylor et al., *Int. Immunol.* 6 (4) 579-591 (1994), Green et al, *Nature Genetics* 7:13-21 (1994), Mendez et al., *Nature Genetics* 15:146-156 (1997), Taylor et al., *Nucleic Acids Research* 20 (23): 6287-6295 (1992), Tuaillon et al., *Proc Natl Acad Sci USA* 90 (8) 3720-3724 (1993), Lonberg et al., *Int Rev Immunol* 13 (1): 65-93 (1995) and Fishwald et al., *Nat Biotechnol* 14 (7): 845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. Sec, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, CA), and Cambridge antibody Technologies (Cambridgeshire, UK). Sec, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, 5427908, 5580717, assigned to Affymax; 5885793, assigned to Cambridge antibody Technologies; 5750373, assigned to Genentech, 5618920, 5595898, 5576195, 5698435, 5693493, 5698417, assigned to Xoma, Colligan, supra; Ausubel, supra; or Sambrook, supra, each of the above patents and publications entirely incorporated herein by reference.

Antibodies used in the method of the present invention can also be prepared using at least one anti-IL23 antibody encoding nucleic acid to provide transgenic animals or mammals, such as goats, cows, horses, sheep, rabbits, and the like, that produce such antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Antibodies used in the method of the present invention can additionally be prepared using at least one anti-IL23 antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. Sec, e.g., Conrad et al., *Plant Mol. Biol.* 38:101-109 (1998) and references cited therein. Thus, antibodies of the present invention can also be produced using transgenic plants, according to known methods. See also, e.g., Fischer et al., Biotechnol. Appl. Biochem. 30:99-108 (October 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. Each of the above references is entirely incorporated herein by reference.

The antibodies used in the method of the invention can bind human IL-23 with a wide range of affinities ($K_D$). In a preferred embodiment, a human mAb can optionally bind human IL-23 with high affinity. For example, a human mAb can bind human IL-23 with a $K_D$ equal to or less than about $10^{-7}$ M, such as but not limited to, 0.1-9.9 (or any range or value therein)$\times10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, NY (1984); Kuby, Janis *Immunology*, W. H. Freeman and Company: New York, NY (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Nucleic Acid Molecules

Using the information provided herein, for example, the nucleotide sequences encoding at least 70-100% of the contiguous amino acids of at least one of the light or heavy chain variable or CDR regions described herein, among other sequences disclosed herein, specified fragments, variants or consensus sequences thereof, or a deposited vector comprising at least one of these sequences, a nucleic acid molecule of the present invention encoding at least one anti-IL-23 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules used in the method of the present invention can include nucleic acid molecules comprising an open reading frame (ORF), optionally, with one or more introns, e.g., but not limited to, at least one specified portion of at least one CDR, such as CDR1, CDR2 and/or CDR3 of at least one heavy chain or light chain; nucleic acid molecules comprising the coding sequence for an anti-IL-23 antibody or variable region; and nucleic acid molecules which comprise a nucleotide sequence substantially different from those described above but which, due to the degeneracy of the genetic code, still encode at least one anti-IL-23 antibody as described herein and/or as known in the art. Of course, the genetic code is well known in the art. Thus, it would be routine for one skilled in the art to generate such degenerate nucleic acid variants that code for specific anti-IL-23 antibodies used in the method of the present invention. See, e.g., Ausubel, et al., supra, and such nucleic acid variants are included in the present invention. Non-limiting examples of isolated nucleic acid molecules include nucleic acids encoding HC CDR1, HC CDR2, HC CDR3, LC CDR1, LC CDR2, and LC CDR3, respectively.

As indicated herein, nucleic acid molecules which comprise a nucleic acid encoding an anti-IL-23 antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Selectively Hybridizing to a Polynucleotide as Described Herein

The method of the present invention uses isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides will encode at least a portion of an antibody. The polynucleotides embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, are well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide used in the method of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, ct al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (Scc, e.g., Ausubel, supra; or Sambrook, supra.)

For instance, polymerase chain reaction (PCR) technology can be used to amplify the sequences of polynucleotides used in the method of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, CA (1990). Commercially available kits for genomic PCR amplification are known in the art. Sec, e.g., Advantage-GC Genomic PCR Kit (Clontech). Additionally, e.g., the T4 gene 32 protein (Bochringer Mannheim) can be used to improve yield of long PCR products.

Synthetic Methods for Constructing Nucleic Acids

The isolated nucleic acids used in the method of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention uses recombinant expression cassettes comprising a nucleic acid. A nucleic acid sequence, for example, a cDNA or a genomic sequence encoding an antibody used in the method of the present invention, can be used to construct a recombinant expression cassette that can be introduced into at least one desired host cell. A recombinant expression cassette will typically comprise a polynucleotide operably linked to transcriptional initiation regulatory sequences that will direct the transcription of the polynucleotide in the intended host cell. Both heterologous and non-heterologous (i.e., endogenous) promoters can be employed to direct expression of the nucleic acids.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide. For example, endogenous promoters can be altered in vivo or in vitro by mutation, deletion and/or substitution.

Vectors and Host Cells

The present invention also relates to vectors that include isolated nucleic acid molecules, host cells that are genetically engineered with the recombinant vectors, and the production of at least one anti-IL-23 antibody by recombinant techniques, as is well known in the art. Sec, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be affected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody used in the method of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein used in the method of the present invention. Alternatively, nucleic acids can be expressed in a host cell by turning on (by manipulation) in a host cell that contains endogenous DNA encoding an antibody. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, Hela cells and the like, which are readily available from, for example, American Type Culture Collection, Manassas, Va (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody

An anti-IL-23 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. Sec, e.g., Colligan, Current Protocols in Immunology, or Current Protocols in Protein Science, John Wiley & Sons, NY, NY, (1997-2001), e.g., Chapters 1, 4, 6, 8, 9, 10, each entirely incorporated herein by reference.

Antibodies used in the method of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-IL-23 Antibodies.

An anti-IL-23 antibody according to the present invention includes any protein or peptide containing molecule that comprises at least a portion of an immunoglobulin molecule, such as but not limited to, at least one ligand binding portion (LBP), such as but not limited to, a complementarity determining region (CDR) of a heavy or light chain or a ligand binding portion thereof, a heavy chain or light chain variable region, a framework region (e.g., FR1, FR2, FR3, FR4 or fragment thereof, further optionally comprising at least one substitution, insertion or deletion), a heavy chain or light chain constant region, (e.g., comprising at least one $C_H1$, hinge1, hinge2, hinge3, hinge4, $C_H2$, or $C_H3$ or fragment thereof, further optionally comprising at least one substitution, insertion or deletion), or any portion thereof, that can be incorporated into an antibody. An antibody can include or be derived from any mammal, such as but not limited to, a human, a mouse, a rabbit, a rat, a rodent, a primate, or any combination thereof, and the like.

The isolated antibodies used in the method of the present invention comprise the antibody amino acid sequences disclosed herein encoded by any suitable polynucleotide, or any isolated or prepared antibody. Preferably, the human antibody or antigen-binding fragment binds human IL-23 and, thereby, partially or substantially neutralizes at least one biological activity of the protein. An antibody, or specified portion or variant thereof, that partially or preferably substantially neutralizes at least one biological activity of at least one IL-23 protein or fragment can bind the protein or fragment and thereby inhibit activities mediated through the binding of IL-23 to the IL-23 receptor or through other IL-23-dependent or mediated mechanisms. As used herein, the term "neutralizing antibody" refers to an antibody that can inhibit an IL-23-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-IL-23 antibody to inhibit an IL-23-dependent activity is preferably assessed by at least one suitable IL-23 protein or receptor assay, as described herein and/or as known in the art. A human antibody can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4 (e.g., γ1, γ2, γ3, γ4). Antibodies of this type can be prepared by employing a transgenic mouse or other trangenic non-human mammal comprising at least one human light chain (e.g., IgG, IgA, and IgM) transgenes as described herein and/or as known in the art. In another embodiment, the anti-IL-23 human antibody comprises an IgG1 heavy chain and an IgG1 light chain.

An antibody binds at least one specified epitope specific to at least one IL-23 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein.

Generally, the human antibody or antigen-binding fragment will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. The CDR sequences may be derived from human germline sequences or closely match the germline sequences. For example, the CDRs from a synthetic library derived from the original non-human CDRs can be used. These CDRs may be formed by incorporation of conservative substitutions from the original non-human sequence. In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3.

Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-IL-23 specific antibody can comprise at least one of a heavy or light chain variable region having a defined amino acid sequence. For example, in a preferred embodiment, the anti-IL-23 antibody comprises at least one of a heavy chain variable region, optionally having the amino acid sequence of SEQ ID NO:7 and/or at least one light chain variable region, optionally having the amino acid sequence of SEQ ID NO:8. In an additional preferred embodiment, the anti-IL-23 antibody comprises at least one heavy chain, optionally having the amino acid sequence of SEQ ID NO:9 and/or at least one light chain, optionally having the amino acid sequence of SEQ ID NO: 10. Antibodies that bind to human IL-23 and that comprise a defined heavy or light chain variable region can be prepared using suitable methods, such as phage display (Katsube, Y., et al., *Int J Mol. Med,* 1 (5): 863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human IL-23 or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human IL-23 with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include, without limitation, replacement of one amino acid by another within the following groups: lysine (K), arginine (R) and histidine (H); aspartate (D) and glutamate (E); asparagine (N), glutamine (Q), serine(S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes

The amino acids that make up anti-IL-23 antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

| SINGLE LETTER CODE | THREE LETTER CODE | NAME | THREE NUCLEOTIDE CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

An anti-IL-23 antibody used in the method of the present invention can include one or more amino acid substitutions, deletions or additions, either from natural mutations or human manipulation, as specified herein.

The number of amino acid substitutions a skilled artisan would make depends on many factors, including those described above. Generally speaking, the number of amino acid substitutions, insertions or deletions for any given anti-IL-23 antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-IL-23 specific antibody that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one IL-23 neutralizing activity. Sites that are critical for antibody binding can also be identified by structural analysis, such as crystallization, nuclear magnetic resonance or photoaffinity labeling (Smith, et al., J. Mol. Biol. 224:899-904 (1992) and de Vos, et al., Science 255: 306-312 (1992)).

Anti-IL-23 antibodies can include, but are not limited to, at least one portion, sequence or combination selected from 5 to all of the contiguous amino acids of at least one of SEQ ID NOS: 1, 2, 3, 4, 5, and 6.

IL-23 antibodies or specified portions or variants can include, but are not limited to, at least one portion, sequence or combination selected from at least 3-5 contiguous amino acids of the SEQ ID NOs above; 5-17 contiguous amino acids of the SEQ ID NOs above, 5-10 contiguous amino acids of the SEQ ID NOs above, 5-11 contiguous amino acids of the SEQ ID NOs above, 5-7 contiguous amino acids of the SEQ ID NOs above; 5-9 contiguous amino acids of the SEQ ID NOs above.

An anti-IL-23 antibody can further optionally comprise a polypeptide of at least one of 70-100% of 5, 17, 10, 11, 7, 9, 119, or 108 contiguous amino acids of the SEQ ID NOs above. In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of the SEQ ID NOs above. For example, the amino acid sequence of a light chain variable region can be compared with the sequence of the SEQ ID NOs above, or the amino acid sequence of a heavy chain CDR3 can be compared with the SEQ ID NOs above. Preferably, 70-100% amino acid identity (i.e., 90, 91, 92, 93, 94, 95, 96, 97, 98, 99, 100 or any range or value therein) is determined using a suitable computer algorithm, as known in the art.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, MD).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12 (1): 387 (1984)), BLASTP, BLASTN, and FASTA (Atschul, S. F. et al., J. Molec. Biol. 215:403-410 (1990)). The BLAST X program is publicly available from NCBI and other sources (BLAST Manual, Altschul, S., et al., NCBINLM NIH Bethesda, Md. 20894: Altschul, S., et al., J. Mol. Biol. 215:403-410 (1990). The well-known Smith Waterman algorithm may also be used to determine identity.

Preferred parameters for polypeptide sequence comparison include the following: (1) Algorithm: Needleman and Wunsch, J. Mol Biol. 48:443-453 (1970) Comparison matrix: BLOSSUM62 from Hentikoff and Hentikoff, Proc. Natl. Acad. Sci, USA. 89:10915-10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide sequence comparisons (along with no penalty for end gaps).

Preferred parameters for polynucleotide comparison include the following:

(1) Algorithm: Needleman and Wunsch, J. Mol Biol. 48:443-453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid sequence comparisons.

By way of example, a polynucleotide sequence may be identical to another sequence, that is 100% identical, or it may include up to a certain integer number of nucleotide alterations as compared to the reference sequence. Such alterations are selected from the group consisting of at least one nucleotide deletion, substitution, including transition and transversion, or insertion, and wherein the alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the sequence by the numerical percent of the respective percent identity (divided by 100) and subtracting that product from the total number of nucleotides in the sequence, or:

n.sub.n.ltorsim.x.sub.n-(x.sub.n.y), wherein n.sub.n is the number of nucleotide alterations, x.sub.n is the total number of nucleotides in sequence, and y is, for instance, 0.70 for 70%, 0.80 for 80%, 0.85 for 85%, 0.90 for 90%, 0.95 for 95%, etc., and wherein any non-integer product of x.sub.n and y is rounded down to the nearest integer prior to subtracting from x.sub.n.

Alterations of a polynucleotide sequence encoding the SEQ ID NOs above may create nonsense, missense or frameshift mutations in this coding sequence and thereby alter the polypeptide encoded by the polynucleotide following such alterations. Similarly, a polypeptide sequence may be identical to the reference sequence of the SEQ ID NOs above, that is be 100% identical, or it may include up to a certain integer number of amino acid alterations as compared to the reference sequence such that the percentage identity is less than 100%. Such alterations are selected from the group consisting of at least one amino acid deletion, substitution, including conservative and non-conservative substitution, or insertion, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the SEQ ID NOs above by the numerical percent of the respective percent identity (divided by 100) and then subtracting that product from the total number of amino acids in the SEQ ID NOs above, or:

n.sub.a.ltorsim.x.sub.a-(x.sub.a.y), wherein n.sub.a is the number of amino acid alterations, x.sub.a is the total number of amino acids in the SEQ ID NOs above, and y is, for instance 0.70 for 70%, 0.80 for 80%, 0.85 for 85% etc., and wherein any non-integer produce of x.sub.a and y is rounded down to the nearest integer prior to subtracting it from x.sub.a.

Exemplary heavy chain and light chain variable regions sequences and portions thereof are provided in the SEQ ID NOs above. The antibodies of the present invention, or specified variants thereof, can comprise any number of contiguous amino acid residues from an antibody of the present invention, wherein that number is selected from the group of integers consisting of from 10-100% of the number of contiguous residues in an anti-IL-23 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and, preferably, at least 50%, 60%, or 70%, and, most preferably, at least 80%, 90%, or 95%-100% or more (including, without limitation, up to 10 times the specific activity) of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone.

Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-9-octadecanoate ($C_{18}$, oleate), all cis-□5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, CA (1996)). An activating group can be bonded directly to the organic group (e.g., hydrophilic polymer, fatty acid, fatty acid ester), or through a linker moiety, for example, a divalent $C_1$-$C_{12}$ group wherein one or more carbon atoms can be replaced by a heteroatom, such as oxygen, nitrogen or sulfur. Suitable linker moieties include, for example, tetraethylene glycol, —$(CH_2)_3$—, —NH—$(CH_2)_6$—NH—, —$(CH_2)_2$—NH-and-$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified antibodies can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.,* 3:147-153 (1992); Werlen et al., *Bioconjugate Chem.,* 5:411-417 (1994); Kumaran et al., *Protein Sci.* 6 (10): 2233-2241 (1997); Itoh et al., *Bioorg. Chem.,* 24 (1): 59-68 (1996); Capellas et al., *Biotechnol. Bioeng.,* 56 (4): 456-463 (1997)), and the methods described in Hermanson, G. T., *Bioconjugate Techniques*, Academic Press: San Diego, CA (1996).

The method of the present invention also uses an anti-IL-23 antibody composition comprising at least one, at least two, at least three, at least four, at least five, at least six or more anti-IL-23 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-IL-23 antibody amino acid sequence selected from the group consisting of 70-100% of the contiguous amino acids of the SEQ ID NOs above, or specified fragments, domains or variants thereof. Preferred anti-IL-23 antibody compositions include at least one or two full length, fragments, domains or variants as at least one CDR or LBP containing portions of the anti-IL-23 antibody sequence described herein, for example, 70-100% of the SEQ ID NOs above, or specified fragments, domains or variants thereof. Further preferred compositions comprise, for example, 40-99% of at least one of 70-100% of the SEQ ID NOs above, etc., or specified fragments, domains or variants thereof. Such composition percentages are by weight, volume, concentration, molarity, or molality as liquid or dry solutions, mixtures, suspension, emulsions, particles, powder, or colloids, as known in the art or as described herein.

Antibody Compositions Comprising Further Therapeutically Active Ingredients

The antibody compositions used in the method of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, 21st edition, Springhouse Corp., Springhouse, PA, 2001; Health Professional's Drug Guide 2001, ed., Shannon, Wilson, Stang, Prentice-Hall, Inc, Upper Saddle River, NJ; Pharmcotherapy Handbook, Wells et al., ed., Appleton & Lange, Stamford, CT, each entirely incorporated herein by reference).

By way of example of the drugs that can be combined with the antibodies for the method of the present invention, the anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The at least one cephalosporin can be at least one selected from cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef.

The at least one coricosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system.

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, and tacrolimus.

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (Sec, e.g., pp. 1098-1136 of *Nursing* 2001 *Drug Handbook.*)

Anti-IL-23 antibody compositions can further comprise at least one of any suitable and effective amount of a composition or pharmaceutical composition comprising at least one anti-IL-23 antibody contacted or administered to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept, CDP-571, CDP-870, afclimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), an immunization, an immunoglobulin, an immunosuppressive (e.g., basiliximab, cyclosporine, daclizumab), a cytokine or a cytokine antagonist. Non-limiting examples of such cytokines include, but are not limited to, any of IL-1 to IL-40 et al. (e.g., IL-1, IL-2, etc.). Suitable dosages are well known in the art. Sec, e.g., Wells et al., eds., Pharmacotherapy Handbook, 2nd Edition, Appleton and Lange, Stamford, CT (2000); PDR Pharmacopoeia, Tarascon Pocket Pharmacopoeia 2000, Deluxe Edition, Tarascon Publishing, Loma Linda, CA (2000), each of which references are entirely incorporated herein by reference.

Anti-IL-23 antibody compounds, compositions or combinations used in the method of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences,* 18th Edition, Mack Publishing Co. (Easton, PA) 1990. Pharmaceutically acceptable carriers can be routinely selected that are suitable for the mode of administration, solubility and/or stability of the anti-IL-23 antibody, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-23 antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, anti-IL-23 antibody compositions can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-IL-23 antibody, portion or variant compositions according to the invention are known in the art, e.g., as listed in "Remington: The Science & Practice of Pharmacy," $19^{th}$ ed., Williams & Williams, (1995), and in the "Physician's Desk Reference," $52^{nd}$ ed., Medical Economics, Montvale, NJ (1998), the disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which may be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one anti-IL-23 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the method of the invention uses an article of manufacture, comprising packaging material and at least one vial comprising a solution of at least one anti-IL-23 specific antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further uses an article of manufacture, comprising packaging material, a first vial comprising lyophilized anti-IL-23 specific antibody, and a second vial comprising an aqueous diluent of prescribed buffer or preservative, wherein said packaging material comprises a label that instructs a patient to reconstitute the anti-IL-23 specific antibody in the aqueous diluent to form a solution that can be held over a period of twenty-four hours or greater.

The anti-IL-23 specific antibody used in accordance with the present invention can be produced by recombinant means, including from mammalian cell or transgenic preparations, or can be purified from other biological sources, as described herein or as known in the art.

The range of the anti-IL-23 specific antibody includes amounts yielding upon reconstitution, if in a wet/dry system, concentrations from about 1.0 μg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol)

or non-ionic surfactants, such as polysorbate 20 or 80 or poloxamer 184 or 188, Pluronic® polyls, other block co-polymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations can be prepared by a process which comprises mixing at least one anti-IL-23 specific antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-23 specific antibody and preservative in an aqueous diluent is carried out using conventional dissolution and mixing procedures. To prepare a suitable formulation, for example, a measured amount of at least one anti-IL-23 specific antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The formulations can be provided to patients as clear solutions or as dual vials comprising a vial of lyophilized anti-IL-23 specific antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present articles of manufacture are useful for administration over a period ranging from immediate to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of anti-IL-23 specific antibody can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-IL-23 specific antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-IL-23 specific antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising single vial systems include pen-injector devices for delivery of a solution, such as BD Pens, BD Autojector®, Humaject®. NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, Smartject® e.g., as made or developed by Becton Dickensen (Franklin Lakes, NJ, www.bectondickenson.com), Disetronic (Burgdorf, Switzerland, www.disetronic.com; Bioject, Portland, Oregon (www.bioject.com); National Medical Products, Weston Medical (Peterborough, UK, www.weston-medical.com), Medi-Ject Corp (Minneapolis, MN, www.mediject.com), and similary suitable devices. Recognized devices comprising a dual vial system include those pen-injector systems for reconstituting a lyophilized drug in a cartridge for delivery of the reconstituted solution, such as the HumatroPen®. Examples of other devices suitable include pre-filled syringes, auto-injectors, needle free injectors, and needle free IV infusion sets.

The products may include packaging material. The packaging material provides, in addition to the information required by the regulatory agencies, the conditions under which the product can be used. The packaging material of the present invention provides instructions to the patient, as applicable, to reconstitute the at least one anti-IL-23 antibody in the aqueous diluent to form a solution and to use the solution over a period of 2-24 hours or greater for the two vial, wet/dry, product. For the single vial, solution product, pre-filled syringe or auto-injector, the label indicates that such solution can be used over a period of 2-24 hours or greater. The products are useful for human pharmaceutical product use.

The formulations used in the method of the present invention can be prepared by a process that comprises mixing an anti-IL-23 antibody and a selected buffer, preferably, a phosphate buffer containing saline or a chosen salt. Mixing the anti-IL-23 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The method of the invention provides pharmaceutical compositions comprising various formulations useful and acceptable for administration to a human or animal patient. Such pharmaceutical compositions are prepared using water at "standard state" as the diluent and routine methods well known to those of ordinary skill in the art. For example, buffering components such as histidine and histidine monohydrochloride hydrate, may be provided first followed by the addition of an appropriate, non-final volume of water diluent, sucrose and polysorbate 80 at "standard state." Isolated antibody may then be added. Last, the volume of the pharmaceutical composition is adjusted to the desired final volume under "standard state" conditions using water as the diluent. Those skilled in the art will recognize a number of other methods suitable for the preparation of the pharmaceutical compositions.

The pharmaceutical compositions may be aqueous solutions or suspensions comprising the indicated mass of each constituent per unit of water volume or having an indicated pH at "standard state." As used herein, the term "standard state" means a temperature of 25° C.+/−2° C. and a pressure of 1 atmosphere. The term "standard state" is not used in the art to refer to a single art recognized set of temperatures or pressure, but is instead a reference state that specifics temperatures and pressure to be used to describe a solution or suspension with a particular composition under the reference "standard state" conditions. This is because the volume of a solution is, in part, a function of temperature and pressure. Those skilled in the art will recognize that pharmaceutical compositions equivalent to those disclosed here can be produced at other temperatures and pressures. Whether such pharmaceutical compositions are equivalent to those disclosed here should be determined under the "standard state" conditions defined above (e.g. 25° C.+/−2° C. and a pressure of 1 atmosphere).

Importantly, such pharmaceutical compositions may contain component masses "about" a certain value (e.g. "about 0.53 mg L-histidine") per unit volume of the pharmaceutical composition or have pH values about a certain value. A component mass present in a pharmaceutical composition or pH value is "about" a given numerical value if the isolated antibody present in the pharmaceutical composition is able to bind a peptide chain while the isolated antibody is present in the pharmaceutical composition or after the isolated antibody has been removed from the pharmaceutical composition (e.g., by dilution). Stated differently, a value, such as a component mass value or pH value, is "about" a given numerical value when the binding activity of the isolated antibody is maintained and detectable after placing the isolated antibody in the pharmaceutical composition.

Competition binding analysis is performed to determine if the IL-23 specific mAbs bind to similar or different epitopes and/or compete with each other. Abs are individually coated on ELISA plates. Competing mAbs are added, followed by the addition of biotinylated hrIL-23. For positive control, the same mAb for coating may be used as the competing mAb ("self-competition"). IL-23 binding is detected using streptavidin. These results demonstrate whether the mAbs recognize similar or partially overlapping epitopes on IL-23.

In one embodiment of the pharmaceutical compositions, the isolated antibody concentration is from about 77 to about 104 mg per ml of the pharmaceutical composition. In another embodiment of the pharmaceutical compositions the pH is from about 5.5 to about 6.5.

The stable or preserved formulations can be provided to patients as clear solutions or as dual vials comprising a vial of lyophilized at least one anti-IL-23 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the anti-IL-23 antibody may result in other than a clear solution of lyophilized powder comprising the antibody. Among non-clear solutions are formulations comprising particulate suspensions, said particulates being a composition containing the anti-IL-23 antibody in a structure of variable dimension and known variously as a microsphere, microparticle, nanoparticle, nanosphere, or liposome. Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymers selected from the group consisting of gleatin agar, starch, arabinogalactan, albumin, collagen, polyglycolic acid, polylactic aced, glycolide-L(−) lactide poly(episilon-caprolactone, poly(epsilon-caprolactone-CO-lactic acid), poly(epsilon-caprolactone-CO-glycolic acid), poly(ß-hydroxy butyric acid), polyethylene oxide, polyethylene, poly (alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(−) lactide poly(episilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds, such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO9916419. The stabilized dispersions may be administered to the lung of a patient using a metered dose inhaler.

Equipment useful in the commercial manufacture of spray dried medicaments are manufactured by Buchi Ltd. or Niro Corp.

An anti-IL-23 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating Crohn's disease, in a cell, tissue, organ, animal, or patient, as known in the art or as described herein, using at least one IL-23 antibody of the present invention, e.g., administering or contacting the cell, tissue, organ, animal, or patient with a therapeutic effective amount of IL-23 specific antibody.

Any method of the present invention can comprise administering an effective amount of a composition or pharmaceutical composition comprising an anti-IL-23 antibody to a cell, tissue, organ, animal or patient in need of such modulation, treatment or therapy. Such a method can optionally further comprise co-administration or combination therapy for treating such diseases or disorders, wherein the administering of said at least one anti-IL-23 antibody, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept (Enbrel™), adalimulab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., cpoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, 2nd Edition, Appleton and Lange, Stamford, CT (2000); PDR Pharmacopocia, Tarascon Pocket Pharmacopoeia 2000, Deluxe Edition, Tarascon Publishing, Loma Linda, CA (2000); Nursing 2001 Handbook of Drugs, 21st edition, Springhouse Corp., Springhouse, PA, 2001; Health Professional's Drug Guide 2001, ed., Shannon, Wilson, Stang, Prentice-Hall, Inc, Upper Saddle River, NJ, each of which references are entirely incorporated herein by reference.

Therapeutic Treatments

Typically, treatment of Crohn's disease is affected by administering an effective amount or dosage of an anti-IL-23 antibody composition that total, on average, a range from at least about 0.01 to 500 milligrams of an anti-IL-23 antibody per kilogram of patient per dose, and, preferably, from at least about 0.1 to 100 milligrams antibody/kilogram of patient per single or multiple administration, depending upon the specific activity of the active agent contained in the composition. Alternatively, the effective serum concentration can comprise 0.1-5000 μg/ml serum concentration per single or multiple administrations. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 μg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or, alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or, alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of an anti-IL-23 antibody. While pulmonary administration is used in the following description, other modes of administration can be used according to the present invention with suitable results. IL-23 specific antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Alternative Delivery

The invention further relates to the administration of an anti-IL-23 antibody by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. An anti-IL-23 antibody composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

Having generally described the invention, the same will be more readily understood by reference to the following Examples, which are provided by way of illustration and are not intended as limiting. Further details of the invention are illustrated by the following non-limiting Examples. The disclosures of all citations in the specification are expressly incorporated herein by reference.

EMBODIMENTS

This invention provides the following non-limiting embodiments:

1. A method of treating Crohn's disease in a patient, comprising administering to the patient an initial subcutaneous dose of 400 mg of an antibody specific to IL23, a 400 mg subcutaneous dose about 4 weeks after the initial dose and a 400 mg subcutaneous dose about 8 weeks after the initial dose.
2. The method of embodiment 1, further comprising administering a dose of 100 mg or 200 mg of antibody about every 4 weeks or about every 8 weeks after the dose at about 8 weeks.
3. The method of embodiment 2, further comprising administering a dose of 200 mg of antibody about every 4 weeks after the dose at about 8 weeks.
4. The method of embodiment 2, further comprising administering a dose of 100 mg of antibody about every 8 weeks after the dose at about 8 weeks.
5. The method of embodiment 1, wherein the patient is a responder to the antibody and is identified as meeting a clinical endpoint about 12 weeks after the initial dose, wherein the clinical endpoint is clinical remission at Week 12, defined as CDAI less than (<) 150 points or endoscopic response measured by at least a 50% improvement from baseline in the Simple Endoscopic Score for Crohn's Disease (SES-CD).

6. The method of embodiment 1, wherein the patient is identified as meeting a clinical endpoint, wherein the clinical endpoint is selected from the group consisting of: (i) clinical remission, defined as CDAI less than (<) 150 points measured at about 24 weeks after the initial dose; (ii) Patient-Reported Outcome (PRO)-2 remission defined based on average daily stool frequency (SF)≤3 and average daily abdominal pain (AP) score≤1 and no worsening of AP or SF from baseline measured at about 12 weeks after the initial dose; and (iii) clinical response, defined as greater than or equal to (≥) 100-point reduction from baseline in CDAI score measured at about 12 weeks after the initial dose.

7. The method of embodiment 1, wherein the antibody comprises a light chain variable region and a heavy chain variable region, said light chain variable region comprising:

a complementarity determining region light chain 1 (CDRL1) amino acid sequence of SEQ ID NO:4;

a CDRL2 amino acid sequence of SEQ ID NO:5; and a CDRL3 amino acid sequence of SEQ ID NO:6, said heavy chain variable region comprising:

a complementarity determining region heavy chain 1 (CDRH1) amino acid sequence of SEQ ID NO:1;

a CDRH2 amino acid sequence of SEQ ID NO:2; and a CDRH3 amino acid sequence of SEQ ID NO:3, and wherein the patient is deemed a responder to the antibody 8. The method of embodiment 7, wherein the patient is a responder to the antibody and is identified as meeting a clinical endpoint shown below:

(i) Change from Baseline in the Crohn's Disease Activity Index (CDAI) Score;

(ii) Clinical remission, defined as CDAI less than (<) 150 points;

(iii) Clinical response, defined as greater than or equal to (>=) 100-point reduction from baseline in CDAI score or CDAI score <150;

(iv) Patient-Reported Outcome (PRO)-2 Remission, defined based on average daily stool frequency (SF) and average daily abdominal pain (AP) score;

(v) Clinical-Biomarker Response, defined using clinical response based on the CDAI score and reduction from baseline in C-reactive protein (CRP) or fecal calprotectin;

(vi) Endoscopic Response, measured by the Simple Endoscopic Score for Crohn's Disease (SES-CD);

(vii) Endoscopic Remission, measured by the Simple Endoscopic Score for Crohn's Disease (SES-CD);

(viii) Durable Clinical Remission at Week 48, defined as CDAI<150 for most of all visits between Week 12 and Week 48;

(ix) Corticosteroid-Free Clinical Remission at Week 48, defined as CDAI score <150 at Week 48 and not receiving corticosteroids at Week 48;

(x) Fatigue response based on the Patient-Reported Outcomes Measurement Information System (PROMIS); and (xi) Endoscopic response measured by the Simple Endoscopic Score for Crohn's Disease (SES-CD).

9. The method of embodiment 8, wherein the clinical endpoint(s) is measured 4, 8, 12, 16, 20, 28, 32, 36, 40, 44 and/or 48 weeks after initial treatment.

10. The method of embodiment 7, wherein the antibody is in a composition comprising 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

11. The method of embodiment 1, further comprising administering to the patient one or more additional drugs used to treat Crohn's disease.

12. The method of embodiment 11, wherein the additional drug is selected from the group consisting of: immunosuppressive agents, non-steroidal anti-inflammatory drugs (NSAIDs), methotrexate (MTX), anti-B-cell surface marker antibodies, anti-CD20 antibodies, rituximab, TNF-inhibitors, corticosteroids, and co-stimulatory modifiers.

13. The method of embodiment 1, wherein the antibody comprises a light chain variable region amino acid sequence of SEQ ID NO: 8 and a heavy chain variable region amino acid sequence of SEQ ID NO: 7.

14. The method of embodiment 1, wherein the antibody comprises a light chain amino acid sequence of SEQ ID NO: 10 and a heavy chain amino acid sequence of SEQ ID NO: 9.

15. The method of embodiment 1, wherein the patient is considered a biologic therapy failure or intolerance for Crohn's disease (Bio-Failure).

16. The method of embodiment 1, wherein the patient is considered a conventional therapy failure or intolerance for Crohn's disease (Con-Failure).

17. The method of embodiment 1, wherein the Crohn's disease is moderately to severely active Crohn's disease.

18. The method of embodiment 17, wherein the patient has endoscopic evidence of active Crohn's disease prior to administration of the initial dose.

19. The method of embodiment 17, wherein the patient has moderately to severely active Crohn's disease for at least three months prior to administration of the initial dose.

20. A method of treating moderately to severely active Crohn's disease in a patient, comprising (i) administering to the patient an initial subcutaneous dose of 400 mg of an antibody specific to IL23, a 400 mg subcutaneous dose about 4 weeks after the initial dose and a 400 mg subcutaneous dose about 8 weeks after the initial dose, and (ii) further administering a dose of 200 mg of antibody about every 4 weeks after the dose at about 8 weeks or a dose of 100 mg of antibody about every 8 weeks after the dose at about 8 weeks, wherein the antibody comprises a light chain variable region amino acid sequence of SEQ ID NO: 8 and a heavy chain variable region amino acid sequence of SEQ ID NO: 7 and the patient is a responder to the antibody by being identified as meeting a clinical endpoint about 12 weeks after the initial dose, wherein the clinical endpoint is clinical remission at Week 12, defined as CDAI less than (<) 150 points or endoscopic response measured by at least a 50% improvement from baseline in the Simple Endoscopic Score for Crohn's Disease (SES-CD).

EXAMPLES

Example 1

Preclinical Evidence Implicating IL-23 as a Target in Crohn's Disease

Genetic and animal model studies have explored the contribution of IL-12 and IL-23 in driving the pathophysiology of Crohn's disease. The results indicate that IL-23 plays a predominant role in inflammatory bowel disease (IBD) and emerging evidence suggests that blocking IL-23 alone may be a more effective strategy than blocking both IL-12 and IL-23.

Initial observations from genetic and animal model data suggest that Crohn's disease is mediated by IL-12 and/or IL-23, potentially through the Th1 and Th 17 pathways they induce, respectively. However, increasing evidence suggests a predominant role for IL-23 in Crohn's disease. Genome-wide association studies identified polymorphisms in the IL-23R gene that are associated with Crohn's disease. The role of IL-23 in driving intestinal inflammation has been shown in several mouse models. Mice treated with anti-IL-23 antibodies exhibited attenuated inflammation, and mice with a genetic deletion of the p19 subunit of IL-23 are protected in several models of intestinal inflammation.

Clinical Experience with IL-12/23-Targeted Therapy (Ustekinumab) in Crohn's Disease The ustekinumab Phase 3 program in Crohn's disease included two 8-week studies evaluating the efficacy and safety of ustekinumab intravenous (IV) induction, and one maintenance study evaluating the efficacy and safety of ustekinumab subcutaneous (SC) maintenance, for a total duration of 52 weeks of treatment. Ustekinumab was evaluated in the full spectrum of biologic-eligible patients with Crohn's disease, i.e., those who were conventional therapy failures and those who were biologic therapy failures. After a single ustekinumab ~6 mg/kg IV induction dose at Week 0, approximately 21% and 40% of BIO-failure and CON-failure participants, respectively (versus approximately 7% and 20% of placebo-treated participants, respectively), achieved clinical remission at Week 8 (as evaluated by the Crohn's Disease Activity Index [CDAI]). Among participants who responded to ustekinumab IV induction and were rerandomized to receive ustekinumab SC maintenance 90 mg every 8 weeks (q8w) or 90 mg every 12 weeks (q12w), approximately 53% and 49% of participants were in clinical remission at Week 52, respectively, compared with 36% of participants who received placebo maintenance.

Clinical Experience with IL-23-Targeted Therapy in Crohn's Disease

The potential therapeutic role of IL-23 in Crohn's disease was first established by clinical studies of IL-12/23p40 antagonists (briakinumab and ustekinumab). Ustekinumab (STELARA®) was recently approved for the treatment of moderately to severely active Crohn's disease. While these programs demonstrated that blockade of both IL-12 and IL-23 is effective in treating Crohn's disease, they could not ascertain the relative contributions of the 2 cytokines.

Recent studies of 2 anti-IL-23 antagonists, risankizumab (previously BI-655066) and brazikumab (formerly MEDI2070, AMG 139), reported Phase 2 results demonstrating efficacy of IL-23 blockade in participants with moderately to severely active Crohn's disease, efficacy in improving clinical signs and symptoms, reducing inflammatory biomarkers, and improving endoscopic findings in participants primarily with biologic-refractory Crohn's disease. The magnitude of efficacy observed in each of these studies suggests the potential for improved efficacy compared with ustekinumab (anti-IL-12/23), recognizing the limitations of cross-study comparisons as well as the comparatively small size of the IL-23 Phase 2 studies.

Cross-study comparisons of clinical remission rates with the IL-23 blockers suggest the potential for improved efficacy compared with ustekinumab. It is notable that the induction doses used in the studies of both risankizumab (200 and 600 mg IV at Weeks 0, 4, 8) and brazikumab (700 mg IV at Weeks 0, 4) were considerably higher than approved ustekinumab dosing (~6 mg/kg IV at Week 0). A cross-compound meta-analysis suggests that the risankizumab dosing, in particular, may be at the higher end of the dose-response curve.

Furthermore, the Phase 2 study with risankizumab also suggested the potential that response rates may not reach maximum until after 6 months of treatment. With doses of 600 mg IV every 4 weeks (q4w) for up to 6 months, clinical remission rates of approximately 50% were observed in all-treated patients, substantially higher than remission rates previously reported for other agents, including ustekinumab, in similar study populations at similar follow-up time points. Of those participants who were in remission at 6 months and who continued risankizumab maintenance treatment (180 mg SC q8w), approximately 70% were in remission at 1 year.

Currently, the GALAXI clinical program is evaluating guselkumab intravenous (IV) induction dosing followed by subcutaneous (SC) maintenance dosing in participants with moderately to severely active Crohn's disease who have demonstrated an inadequate response or failure to tolerate previous conventional therapy or biologic therapy. Under the GALAXI protocol, there are 3 separate studies (Phase 2 study GALAXI 1 and Phase 3 studies GALAXI 2 and GALAXI 3). Results from the GALAXI I study show that guselkumab IV induction demonstrated greater improvements compared to placebo across the key clinical efficacy and endoscopic outcome measures at Week 12.

Overall Rationale for Guselkumab in Crohn's Disease

In summary, the collective genetic and preclinical evidence implicates the prominent role of selectively targeting IL-23 in modulating the underlying pathophysiology of IBD. The available clinical experience of 2 IL-23 antagonists and the established evidence from an approved IL-12/23 antagonist (ustekinumab) have demonstrated proof of mechanism and proof of concept, respectively, for targeting IL-23 in the treatment of Crohn's disease. Together, the available evidence provide support for investigating guselkumab in the treatment of Crohn's disease.

In the current study, the sponsor is interested in assessing SC administration of guselkumab for the induction phase of Crohn's disease treatment. Subcutaneous delivery of biologic agents has become a valuable alternative to IV administration across many disease areas. Although the pharmacokinetic (PK) profiles of SC and IV routes of administrations differ, SC administration has proven effective, safe, well-tolerated, and is generally preferred by patients and healthcare providers due to the greater flexibility and ease of administration for patients or their caregivers in their preferred setting. In addition, SC administration has resulted in reduced drug delivery-related healthcare costs and resource utilization. In short, SC administration has become an attractive alternative to more invasive and time-consuming IV infusions.

Considering the GALAXI 1 results and the potential benefits of SC induction dosing to patients and healthcare systems, the aim of this study is to evaluate the efficacy, safety, and PK/pharmacodynamics (PD) profile of guselkumab SC induction compared with placebo in participants with moderately to severely active Crohn's disease.

Clinical Protocol

Protocol Title—GRAVITI

A Randomized, Double-blind, Placebo-controlled, Parallel-group, Multicenter Study to Evaluate the Efficacy and Safety of Guselkumab Subcutaneous Induction Therapy in Participants With Moderately to Severely Active Crohn's Disease Synopsis Short Title: A Phase 3 Study to Evaluate the Efficacy and Safety of Guselkumab Subcutaneous Induction Therapy in Participants with Moderately to Severely Active Crohn's Disease The term "study intervention" throughout the protocol, refers to study drug.

Objectives and Endpoints

The objectives of this study are to assess the effects ofguselkumab SC in moderately to severely active Crohn's disease. The endpoints at Week 12 will be based on comparisons of the combined guselkumab induction dose group (who received guselkumab 400 mg SC at Weeks 0, 4, and 8) with the placebo group. Week 24 endpoints will be based on comparisons of each guselkumab group (guselkumab 400 mg SC at Weeks 0, 4, and 8, followed by guselkumab 200 mg SC every 4 weeks [q4w] in one group and 100 mg SC every 8 weeks [q8w] in the other group) with the placebo group. The tertiary endpoints include but are not limited to the endpoints specified below. Analyses will be performed at applicable timepoints through Week 24.

TABLE 1

| Objectives | Endpoints |
|---|---|
| **Primary** | |
| To evaluate the efficacy, including clinical remission and endoscopic response, of guselkumab SC induction | Clinical remission (CDAI score <150) at Week 12<br>Endoscopic response (≥50% improvement from baseline in the SES-CD score) at Week 12 |
| **Secondary** | |
| To evaluate the efficacy of guselkumab SC across a range ofoutcome measures | Clinical remission at Week 24<br>PRO-2 remission (an AP mean daily score ≤1 and SF mean daily score ≤3 and no worsening of AP or SF from baseline) at Week 12<br>Clinical response (decrease from baseline in CDAI ≥100 points or clinical |
| To evaluate the safety of guselkumab SC | Summary of AEs, such as SAEs and AEs leading to discontinuation of study intervention |
| **Tertiary (analyses at applicable time points through Week 24)** | |
| To evaluate the efficacy of guselkumab SC across a range ofoutcome measures | Clinical remission<br>PRO-2 remission<br>Clinical response<br>Corticosteroid-free clinical remission<br>Change in CDAI score from baseline<br>AP and SF score, and change in AP and SF score from baseline<br>Change in SES-CD score from baseline<br>Endoscopic remission<br>Endoscopic healing<br>Change in histologic assessments from baseline |
| To evaluate the impact of guselkumab SC on biomarkers | Change in CRP and fecal calprotectin from baseline<br>Clinical-biomarker response |
| To evaluate the PK and immunogenicity of guselkumab SC | Serum concentrations of guselkumab<br>Incidence and titers of antibodies to guselkumab |

TABLE 1-continued

| Objectives | Endpoints |
|---|---|
| To evaluate the impact of guselkumab SC on PROs | Endpoints based on IBDQ, PROMIS-29, AP-NRS, and BSFS |

Abbreviations:
AE = adverse event;
AP = abdominal pain;
AP-NRS = Abdominal Pain-Numerical Rating Scale;
BSFS = Bristol Stool Form Scale;
CDAI = Crohn's Disease Activity Index;
CRP = C-reactive protein;
IBDQ = Inflammatory Bowel Disease Questionnaire;
PK = pharmacokinetic(s);
PRO = Patient-reported Outcome;
PROMIS = Patient-reported Outcomes Measurement Information System;
SAE = serious adverse event;
SC = subcutaneous;
SES-CD = Simple Endoscopic Score for Crohn's Disease;
SF = stool frequency Hypotheses The co-primary hypotheses of this study are that guselkumab is superior to placebo in inducing clinical remission at Week 12 and guselkumab is superior to placebo in inducing endoscopic response at Week 12 among participants with moderately to severely active Crohn's disease.

Overall Design

This is a randomized, double-blind, placebo-controlled, parallel-group, multicenter study to evaluate the efficacy and safety of guselkumab subcutaneous (SC) induction dosing. The target population is adult participants with moderately to severely active Crohn's disease (of at least 3 months duration) with colitis, ileitis, or ileocolitis previously confirmed by radiography, histology, and/or endoscopy. To be eligible for the study, participants must also have endoscopic evidence of active Crohn's disease and have demonstrated an inadequate response or failure to tolerate previous conventional therapy (oral corticosteroids or the immunomodulators azathioprine [AZA], 6-mercaptopurine [6-MP] or methotrexate [MTX]; CON-Failure) or biologic therapy (infliximab, adalimumab, certolizumab pegol, vedolizumab, or approved biosimilars for these agents; BIO-Failure).

The two groups based on prior therapies comprising the target population are briefly described below.

Conventional Therapy Failure or Intolerance (CON-Failure)

Participants must have demonstrated an inadequate response to, or have failed to tolerate, at least 1 of the following conventional Crohn's disease therapies: oral corticosteroids (including prednisone, budesonide, and beclomethasone dipropionate) or the immunomodulators azathioprine (AZA), 6-mercaptopurine (6-MP) or methotrexate (MTX).

Participants who have demonstrated corticosteroid dependence (i.e., an inability to successfully taper corticosteroids without a return of the symptoms of Crohn's disease) are also eligible.

Participants may either be naïve to biologic therapy (i.e., infliximab, adalimumab, certolizumab pegol, vedolizumab, or approved biosimilars for these agents) or may have been exposed to biologic therapy and have not demonstrated inadequate response or intolerance.

Biologic Therapy Failure or Intolerance (BIO-Failure)

Participants must have demonstrated an inadequate response to, or have failed to tolerate, at least 1 or more biologic therapies (i.e., infliximab, adalimumab, certolizumab pegol, vedolizumab, or approved biosimilars for these agents) at a dose that is, at minimum, a locally approved dose for the treatment of Crohn's disease. Inadequate response is defined as: primary nonresponse (i.e., no initial response) or secondary nonresponse (i.e., response initially but subsequently lost response).

Participants with prior exposure to IL-12/23 or IL-23 agents are ineligible for this study.

Overall, the study will evaluate guselkumab SC treatment through 12 weeks of induction therapy and at least 12 weeks of maintenance therapy. At Week 24, all participants will enter the extension phase and receive the same treatment regimen that they were receiving at Week 24. The study will be unblinded after the last participant completes the Week 48 evaluations and the Week 48 database lock (DBL) is completed. Upon study unblinding, placebo participants who have not been rescued with guselkumab will be discontinued from study intervention and have a final efficacy and safety (FES) follow-up visit. All other participants will continue on guselkumab treatment through Week 96.

The overall study duration is up to 109 weeks. The study comprises of the following phases:

1. Screening phase: up to 5 weeks
2. Main treatment phase: 24 weeks
3. Extension treatment phase: 72 weeks
4. Post-treatment phase (FES follow-up visit): until approximately 12 weeks after the last dose of study intervention In general, participants who are receiving oral 5-aminosalicylic acid compounds, oral corticosteroids, conventional immunomodulators (AZA, 6-MP, or MTX), antibiotics, and/or enteral nutrition for the treatment of Crohn's disease at baseline should maintain a stable dose for a specified period before baseline and through Week 48, with the exception of oral corticosteroids. Starting at Week 12, all participants who were taking corticosteroids at Week 0 must begin tapering their corticosteroid dose. This tapering is mandatory, unless not medically feasible. Participants who discontinue study intervention early should return for a study intervention discontinuation (SID) visit. All randomized participants should complete the FES follow-up visit approximately 12 weeks after the last dose of study intervention.

Efficacy, safety, pharmacokinetics (PK), immunogenicity, and biomarkers will be assessed according to the Schedule of Activities (SoA). A blood sample for pharmacogenomic research will be collected only from participants who consent to this component of the protocol (where local regulations permit).

Database locks are planned for Week 24, Week 48, and when the last participant completes the last scheduled assessment as shown in the SoA. Additional DBLs may be added as necessary.

Number of Participants

The target sample size is 318 participants. Participants who had an inadequate response or failure to tolerate biologic therapy will comprise approximately 35% to 65% of the population.

Intervention Groups and Duration

The overall study duration is up to 109 weeks. The study comprises of the following phases:

1. Screening phase: up to 5 weeks
2. Main treatment phase: 24 weeks
3. Extension treatment phase: 72 weeks
4. Post-treatment phase (FES follow-up visit): until approximately 12 weeks after the last dose of study intervention At Week 0, eligible participants will be randomly assigned in a 1:1:1 ratio to one of the following SC treatments:

106 participants to guselkumab 400 mg SC at Weeks 0, 4, and 8 followed by guselkumab 200 mg SC every 4 weeks (q4w) through Week 24

106 participants to guselkumab 400 mg SC at Weeks 0, 4, and 8 followed by guselkumab 100 mg SC every 8 weeks (q8w) through Week 24

106 participants to placebo SC q4w from Week 0 through Week 24

Table 2 is a description of the study interventions.

TABLE 2

| Intervention Name | Guselkumab | Guselkumab | Placebo |
|---|---|---|---|
| Dose Formulation | Active guselkumab 200 mg/2 mL in a single-dose PFS-Y | Active guselkumab 100 mg/1 mL in a single-dose PFS-U | Matching placebo for each dose and device (2 mL PFS-Y and 1 mL PFS-U) |
| Unit Dose Strength(s) | SC 200 mg | SC 100 mg | Matching placebo for each dose and device |
| Frequency | q4w | q8w | Placebo will be administered at the same frequency as the active groups. |
| Route of Administration | SC | SC | SC |
| Storage | Must be stored at controlled temperatures ranging from 36° F. to 46° F. (2° C. to 8° C.) and protected from exposure to light. The sterile product does not contain preservatives and is designed for single use only. It should be clear to slightly yellow and may contain tiny white or clear particles. Do not use if the liquid is cloudy or discolored or has large particles. Protection from light is not required during the preparation and administration of the study intervention material. Aseptic procedures must be used during the preparation and administration of the study intervention material. | Must be stored at controlled temperatures ranging from 36° F. to 46° F. (2° C. to 8° C.) and protected from exposure to light. The sterile product does not contain preservatives and is designed for single use only. It should be clear to slightly yellow and may contain tiny white or clear particles. Do not use if the liquid is cloudy or discolored or has large particles. Protection from light is not required during the preparation and administration of the study intervention material. Aseptic procedures must be used during the preparation and administration of the study intervention material. | Must be stored at controlled temperatures ranging from 36° F. to 46° F. (2° C. to 8° C.) and protected from exposure to light. The sterile product does not contain preservatives and is designed for single use only. It should beclear to slightly yellow and may contain tiny white or clear particles. Do not use if the liquid is cloudy or discolored or has large particles.Protection from light is not required during the preparation and administration of the study intervention material. Aseptic procedures must be used during the preparation and administration of the study intervention material. |
| Use | Experimental | Experimental | Placebo comparator |
| IMP | Yes | Yes | Yes |
| NIMP | No | No | No |

Abbreviations:
IMP = Investigational Medicinal Product;
NIMP = Non-investigational Medicinal Product;
PFS-U = prefilled syringe with an UltraSafe PlusTM Passive Needle Guard;
PFS-Y = prefilled syringe with YpsoMate autoinjector;
q4w = every 4 weeks;
q8w = every 8 weeks;
SC = subcutaneous The randomization will be stratified by baseline Crohn's Disease Activity Index (CDAI) score (≤300 or >300), baseline Simple Endoscopic Score for Crohn's Disease (SES-CD) score (≤12 or >12), and BIO-Failure status (Yes or No) at baseline (Week 0).

During the extension phase, all participants will continue to receive the same treatment regimen that they were receiving at Week 24.

Upon study unblinding after Week 48 DBL, placebo participants who have not been rescued with guselkumab will be discontinued from study intervention and have an FES follow-up visit. All other participants will continue on guselkumab treatment through Week 96.

All participants in the placebo group who meet at least 1 of the rescue criteria at Weeks 12 and 16 will receive rescue treatment, i.e., guselkumab 400 mg SC at Weeks 16, 20, and 24 followed by guselkumab 100 mg SC every 8 weeks (q8w). To maintain the blind, participants randomized to guselkumab who meet at least 1 of the rescue criteria will continue their assigned treatment regimen and receive blinded sham rescue matching placebo SC injection.

In the maintenance study of the ustekinumab Phase 3 Crohn's disease program (IM-UNITI), the sponsor assessed the effect of a single dose adjustment of ustekinumab (an IL-12/23 antagonist) in participants with Crohn's disease. Participants were randomized to receive placebo, ustekinumab 90 mg q12w, or ustekinumab 90 mg q8w (approved dose). In the ustekinumab 90 mg q8w group, 28 participants met pre-specified loss of response criteria and received a sham dose adjustment. After 16 weeks, 32.1% were in clinical remission and 46.4% were in clinical response 16 weeks later. These results demonstrate that some participants with inadequate/loss of clinical response might benefit from continuing on the same dose regimen over time. Therefore, the guselkumab groups in this study will not receive a dose adjustment, but will receive a blinded sham rescue.

A single SC induction guselkumab dose regimen (400 mg SC at Weeks 0, 4, and 8) was selected for this study based on data from the Phase 2 dose-ranging study of guselkumab IV in Crohn's disease (GALAXI 1). The GALAXI 1 Week 12 analyses demonstrated similar efficacy with guselkumab induction doses of 1200 mg, 600 mg, and 200 mg administered IV at Weeks 0, 4, and 8, respectively. There was no clear dose/exposure-response within the range of guselkumab IV induction doses tested. As a result, the 200 mg IV induction dose regimen was selected for confirmatory evaluation in the guselkumab Phase 3 studies (GALAXI 2 and 3).

With an estimated bioavailability of approximately 50% for guselkumab SC (TREMFYA® SmPC 2021; TREMFYA® USPI 2020), a 400 mg SC dose of guselkumab is expected to result in comparable overall guselkumab exposure (AUC) to the 200 mg IV dose. Population PK modeling and simulation demonstrate that while peak concentrations were higher with the 200 mg IV induction dose regimen, trough concentrations following the 400 mg SC induction dose regimen were non-inferior when compared with the IV induction dose regimen. Experience from biologics approved for both IV and SC administration demonstrate that achieving similar overall exposure (average steady-state serum study intervention concentration [Cavg.ss]) with non-inferior trough concentrations results in comparable efficacy for both routes of administration. In addition, serum peak concentrations in the induction period may not be a dominant driver of efficacy for biologics in IBD. Given this, a single guselkumab induction dose regimen of 400 mg SC at Weeks 0, 4, and 8 will be evaluated in participants with moderately to severely active Crohn's disease.

Two guselkumab maintenance dose regimens (200 mg SC q4w and 100 mg SC q8w) will be evaluated in this study. These are the same doses being evaluated in the ongoing Phase 3 GALAXI studies. The selection of the same maintenance dose regimens will enable cross-study comparison of SC induction followed by SC maintenance regimen (in this study) versus IV induction followed by SC maintenance regimen (in GALAXI studies). Overall, the 2 guselkumab maintenance dose regimens (i.e., 200 mg SC q4w and 100 mg SC q8w) would provide an approximately 4-fold dose range of exposure that should support dose/exposure-response assessment of maintenance therapy in the treatment of Crohn's disease.

Randomization will be used to minimize bias in the assignment of participants to intervention groups, to increase the likelihood that known and unknown participant attributes (e.g., demographic and baseline characteristics) are evenly balanced across intervention groups, and to enhance the validity of statistical comparisons across intervention groups. In addition, to minimize imbalance between intervention groups, randomization will be stratified by factors that influence prognosis or treatment response (i.e., stratified at baseline-by-baseline CDAI score, SES-CD score, and BIO-Failure status).

Screening for eligible participants will be performed within 5 weeks before administration of the study intervention. The inclusion and exclusion criteria for enrolling participants in this study are described below.

Inclusion Criteria

Each potential participant must satisfy all of the following criteria to be enrolled in the study:

1. Man or woman (according to their reproductive organs and functions assigned by chromosomal complement) of ≥18 years of age (or the legal age of consent in the jurisdiction in which the study is taking place).
2. Have Crohn's disease or fistulizing Crohn's disease of at least 3 months duration (defined as a minimum of 12 weeks), with colitis, ileitis, or ileocolitis, confirmed at any time in the past by radiography, histology, and/or endoscopy.
3. Have clinically active Crohn's disease, defined as a baseline CDAI score ≥220 but ≤450 and either:
   a. Mean daily SF count ≥4, based on the unweighted CDAI component of the number of liquid or very soft stools

OR b. Mean daily AP score ≥2, based on the unweighted CDAI component of AP
4. Have endoscopic evidence of active ileocolonic Crohn's disease as assessed by central endoscopy reading at the screening endoscopy defined as a screening SES-CD score ≥6 (or ≥4 for participants with isolated ileal disease), based on the presence of ulceration in at least 1 of the 5 ileocolonic segments, resulting in the following specified ulceration component scores:
   a. A minimum score of 1 for the component of "size of ulcers"

AND b. A minimum score of 1 for the component of "ulcerated surface"
5. A participant who has had extensive colitis for ≥8 years, or disease limited to a segment of the colon for ≥10 years, must:

a. Have had a full colonoscopy to assess for the presence of dysplasia within 1 year before the first dose of study intervention

OR b. Has a full colonoscopy with biopsy surveillance for dysplasia as the baseline endoscopy during the screening period. Results from these surveillance biopsies must be negative for dysplasia (low-grade, high-grade, or "indefinite dysplasia in reactive atypia") prior to the first dose of study intervention Concomitant or Previous Medical Therapies Received 6. Prior or current medication for Crohn's disease must include at least 1 of the following:

a. Current treatment with oral corticosteroids (including budesonide and beclomethasone dipropionate) and/or immunomodulators (AZA, 6-MP, MTX)

OR b. History of failure to respond to, or tolerate, at least 1 of the following therapies: oral corticosteroids (including budesonide and beclomethasone dipropionate) or immunomodulators (AZA, 6-MP, MTX)

OR c. History of corticosteroid dependence (i.e., an inability to successfully taper corticosteroids without a return of the symptoms of Crohn's disease)

OR d. Has previously demonstrated lack of initial response (i.e., primary nonresponders), responded initially but then lost response with continued therapy (i.e., secondary nonresponders), or were intolerant to 1 or more biologic agents at a dose that is, at minimum, a locally approved dose for the treatment of Crohn's disease (i.e., infliximab, adalimumab, certolizumab pegol, vedolizumab, or approved biosimilars for these agents)

Note: Participants meeting criteria 6a-c may either be naïve to biologic therapy (i.e., infliximab, adalimumab, certolizumab pegol, vedolizumab, or approved biosimilars for these agents) or may have been exposed to these biologic therapies and did not demonstrate an inadequate response or intolerance.

7. Adhere to all of the following requirements for concomitant medication for the treatment of Crohn's disease. The following medications are permitted provided that doses meeting the requirements listed below are stable or have been discontinued prior to baseline within the timeframes specified below:

a. Oral 5-ASA compounds on stable doses for at least 2 weeks; or if recently discontinued, must have been stopped for at least 2 weeks.

b. Oral corticosteroids at a prednisone-equivalent dose at or below 40 mg/day, or 9 mg/day of budesonide, or 5 mg/day beclomethasone dipropionate, and on stable dosing for at least 2 weeks; or if recently discontinued, must have been stopped for at least 2 weeks.

c. Conventional immunomodulators (i.e., AZA, 6-MP, or MTX) for at least 12 weeks and have been on a stable dose for at least 4 weeks; or if recently discontinued, must have been stopped for at least 4 weeks.

d. If receiving antibiotics as a primary treatment of Crohn's disease, doses must be stable for at least 3 weeks; or if recently discontinued, must have been stopped for at least 3 weeks.

e. If receiving enteral nutrition as a primary treatment for Crohn's disease, must have been receiving for at least 2 weeks; or if recently discontinued, must have been stopped for at least 2 weeks.

Screening Laboratory Tests

8. Have screening laboratory test results within the following parameters, and if 1 or more of the laboratory parameters are out of range, a single retest of laboratory values is permitted during the approximately 5-week screening period:

a. Hemoglobin ≥8.0 g/dL b. White blood cells (WBCs) ≥3.0×103/μL c. Neutrophils ≥1.5×103/μL d. Platelets ≥100×103/μL e. Serum creatinine ≤1.5 mg/dL f. Alanine transaminase (ALT) (or aspartate transaminase [AST])≤2×upper limit of normal (ULN)

g. Total bilirubin (TBili)≤1.5×ULN (Isolated total bilirubin >1.5×ULN is allowed for those participants with known Gilbert's syndrome. Gilbert's syndrome is suggested by direct bilirubin <30%.)

Tuberculosis

A potential participant is considered eligible if the participant meets all of the following TB screening criteria:

Note: Interferon gamma release assay (IGRA) testing includes either QuantiFERON-TB® or T-SPOT®.TB.

a. Have no history of active TB or show signs or symptoms suggestive of active TB upon medical history and/or physical examination at screening.

b. Have no history of latent TB prior to screening. An exception is made for participants who have a history of latent TB AND who satisfy one of the following criteria:

1. Currently receiving treatment for latent TB

OR

2. Will initiate treatment for latent TB prior to the first administration of study intervention Note: For participants with a history of treated latent TB there must be documentation of appropriate treatment prior to the first administration of study intervention. It is the responsibility of the investigator to verify the adequacy of previous TB treatment and provide appropriate documentation. IGRA testing is not required at screening for participants with a history of treated latent TB or ongoing treatment for latent TB.

c. Have had no recent close contact with a person with active TB. If there has been contact, such participants are referred to a physician specializing in TB to determine if treatment is warranted or not. This evaluation must be adequately documented and, if treatment is recommended, the participant must be receiving appropriate treatment prior to the first administration of study intervention.

d. Have a negative IGRA test result within 2 months prior to the first administration of study intervention, or who:

1. Have a history of adequately treated latent TB described above.

2. Have a newly identified positive IGRA test result in which active TB has been ruled out and for which appropriate treatment for latent TB has been initiated prior to the first administration of study intervention.

3. Have a false-positive IGRA test as determined by the following:

A suspected false-positive initial IGRA test must be repeated. Ifr epeat testing is NOT positive, the participant must be referred to a physician specializing in TB to determine if the initial test can be considered a false-positive. This evaluation must be adequately documented prior to the first administration of study intervention. If repeat testing is positive, however, it will be considered a true-positive and the participant is only eligible if active TB has been ruled out and appropriate treatment for latent TB has been initiated as described above.

Note: Indeterminate/borderline results should be handled e. Have a chest radiograph (both posterior-anterior and lateral views, or per local/country regulations where applicable), or chest computed tomography (CT) within 3 months prior to the first administration of study intervention that shows no abnormalities suggestive of active or inactive TB.

Contraception

9. A woman of childbearing potential must have a negative serum pregnancy test result at screening.
10. Before randomization, a woman must be
    a. Not of childbearing potential
    OR
    b. Of childbearing potential and
    If heterosexually active, practicing a highly effective method of contraception (failure rate of <1% per year when used consistently and correctly) and agrees to remain on a highly effective method while receiving study intervention and until 12 weeks after last dose—the end of relevant systemic exposure. Note: The method selected must meet local/regional regulations/guidelines for highly effective contraception.

Note: If a participant's childbearing potential changes after start of the study (e.g., a premenarchal woman experiences menarche) or the risk of pregnancy changes (e.g., a woman who is not heterosexually active becomes active), a woman must begin using a highly effective method of contraception.
11. A woman must agree not to donate eggs (ova, oocytes) for the purposes of assisted reproduction during the study and for a period of 12 weeks after the last administration of study intervention.
12. During the study and for at least 12 weeks after the last administration of study intervention, a male participant:
    a. Who is sexually active with a female of childbearing potential must agree to use a barrier method of contraception (i.e., condom with spermicidal foam/gel/film/cream/suppository or female condom/occlusive cap [diaphragm or cervical/vault caps] with spermicidal foal/gel/film/cream/suppository)
    b. Who is sexually active with a pregnant female must use a condom
13. Must agree not to donate sperm for the purpose of reproduction. Each participant must sign an informed consent form (ICF) indicating that he or she understands the purpose of, and procedures required for, the study and is willing to participate in the study.

Note: In regions where the legal age of consent is older than 18 years, informed consent must be obtained from and signed by both the participant and his or her legally acceptable representative.
14. Must sign a separate ICF if he or she agrees to provide an optional DNA sample for research (where local regulations permit). Refusal to give consent for the optional DNA research sample does not exclude a participant from participation in the study.

Note: In regions where the legal age of consent is older than 18 years, informed consent must be obtained from and signed by both the participant and his or her legally acceptable representative.
15. Be willing and able to adhere to all specified requirements, including but not limited to completion of assessments, adherence to visit schedule, and compliance with the lifestyle restrictions.

Exclusion Criteria

Any potential participant who meets any of the following criteria will be excluded from participating in the study:

1. Has complications of Crohn's disease, such as symptomatic strictures or stenoses, short gut syndrome, or any other manifestation, that might be anticipated to require surgery, could preclude the use of the CDAI to assess response to therapy, or would possibly confound the ability to assess the effect of treatment with guselkumab.
2. Currently has or is suspected to have an abscess. Recent cutaneous and perianal abscesses are not exclusionary if drained and adequately treated at least 3 weeks before baseline, or 8 weeks before baseline for intra-abdominal abscesses, provided that there is no anticipated need for any further surgery. Participants with active fistulas may be included if there is no anticipation of a need for surgery and no abscesses are currently identified.
3. Has had any kind of bowel resection within 24 weeks, or any other intra-abdominal or other major surgery within 12 weeks, before first dose of study intervention.
4. Has a draining (i.e., functioning) stoma or ostomy.
5. Presence on screening endoscopy of adenomatous colonic polyps, if not removed before study entry, or history of adenomatous colonic polyps that were not removed.
6. Has a stool culture or other examination positive for an enteric pathogen, including Clostridioides dificile (formerly known as *Clostridium* dificile) toxin, within 4months before the first dose of study intervention, unless a repeat examination is negative and there are no signs of ongoing infection with that pathogen.

Note: Treatment and repeat testing can occur in the current screening period.

Concomitant or Previous Medical Therapies Received

7. Has received any of the following prescribed medications or therapies within the specified period:
   a. IV corticosteroids received within 3 weeks of baseline
   b. Cyclosporine, tacrolimus, sirolimus, or mycophenolate mofetil received within 8 weeks of baseline
   c. 6-thioguanine received within 4 weeks of baseline
   d. Biologic agents:
      1. Anti-TNFα therapy (e.g., infliximab, etanercept, certolizumab pegol, adalimumab, golimumab) received within 8 weeks of baseline
      2. Vedolizumab received within 12 weeks of baseline
      3. Other immunomodulatory biologic agents, including approved and investigational biologic agents, received within 12 weeks of baseline or within 5 half-lives of baseline, whichever is longer
   e. Any investigational intervention received within 4 weeks of baseline or within 5 half-lives of baseline, whichever is longer.
   f. Non-autologous stem cell therapy (e.g., Prochymal), natalizumab, efalizumab, or biologic agents that deplete B- or T-cells (e.g., rituximab, alemtuzumab, or visilizumab) received within 12 months of baseline.

g. Treatment with apheresis (e.g., Adacolumn apheresis) or total parenteral nutrition for Crohn's disease within 3 weeks of baseline.

8. Has previously received a biologic agent targeting IL-12/23 or IL-23, including but not limited to ustekinumab, briakinumab, brazikumab, guselkumab, mirikizumab, and risankizumab.

Infections or Predisposition to Infections:

9. Has a history of latent or active granulomatous infection, including histoplasmosis or coccidioidomycosis, before screening. Participants with radiographic evidence of possible prior histoplasmosis or coccidioidomycosis will be excluded.

10. Has a history of, or ongoing, chronic or recurrent infectious disease, including but not limited to, sinopulmonary infections, bronchiectasis, recurrent renal/urinary tract infections (e.g., pyelonephritis, cystitis), an open, draining, or infected skin wound, or an ulcer.

11. Chest radiograph must be obtained within 12 weeks before the first dose of study intervention. Results that show an abnormality suggestive of an undiagnosed pulmonary pathology including but not limited to a malignancy, a previously unrecognized pulmonary pathology, as well as active or latent infections from TB, histoplasmosis, or coccidiomycosis would be exclusionary. A chest CT scan obtained outside of the protocol instead of a chest radiograph is also acceptable. Refer to inclusion criteria 9 for information regarding eligibility with a history of latent TB.

12. History of human immunodeficiency virus (HIV) antibody positive, or tests positive for HIV at screening.

13. Is seropositive for antibodies to hepatitis C virus (HCV), unless they satisfy one of the following conditions:

a. Has a history of successful treatment, defined as being negative for HCV RNA at least 12 weeks after completing antiviral treatment, and has a negative HCV RNA test result at screening,
   OR b. While seropositive has a negative HCV RNA test result at least 12 weeks prior to screening and a negative HCV RNA test result at screening.

14. Tests positive for hepatitis B virus (HBV) infection (Appendix 4 [Section 10.4]).

Note: For participants who are not eligible for this study due to HIV, HCV, or HBV test results, consultation with a physician with expertise in the treatment of those infections is recommended.

15. Bacille Calmette-Guérin (BCG) vaccination within 12 months or any other live bacterial or live viral vaccination within 4 weeks prior to screening, or plans to receive such vaccines during the study.

16. Has or has had a nontuberculous mycobacterial infection or clinically significant opportunistic infection (e.g., cytomegalovirus colitis, pneumocystosis, invasive aspergillosis).

17. Has had a clinically significant infection (i.e., hepatitis, sepsis, pneumonia, or pyelonephritis), has been hospitalized for an infection, or has been treated with parenteral antibiotics for an infection within 8 weeks before the first dose of study intervention. Treated and resolved infections not considered clinically significant at the discretion of the investigator need not be exclusionary (i.e., acute upper respiratory tract infection, uncomplicated urinary tract infection).

18. Has current signs or symptoms of a clinically significant infection. Ongoing infections not considered clinically significant at the discretion of the investigator need not be exclusionary (i.e., acute upper respiratory tract infection, uncomplicated urinary tract infection).

19. Has evidence of herpes zoster infection within 8 weeks before the first dose of study intervention.

20. During the 6 weeks prior to baseline, have had ANY of (a) confirmed severe acute respiratory syndrome coronavirus-2 (SARS-COV-2) (Coronavirus Disease 2019 [COVID-19]) infection (test positive), OR (b) suspected SARS-COV-2 infection (clinical features without documented test results), OR (c) close contact with a person with known or suspected SARS-COV-2 infection Exception: May be included with a documented negative result for a validated SARS-COV-2 test a. Obtained at least 2 weeks after conditions (a), (b), (c) above (timed from resolution of key clinical features if present, e.g., fever, cough, dyspnea) AND b. With absence of ALL conditions (a), (b), (c) above during the period between the negative test result and the baseline study visit Note on COVID-19-related exclusion:

The field of COVID-19-related testing (for presence of, and immunity to, the SARS-COV-2 virus) is rapidly evolving. Additional testing may be performed as part of screening and/or during the study if deemed necessary by the investigator and in accordance with current regulations/guidance from authorities/standards of care.

Precaution: for those who may carry a higher risk for severe COVID-19 illness, follow guidance from local health authorities when weighing the potential benefits and risks of enrolling in the study, and during participation in the study.

Malignancy or Increased Potential for Malignancy:

21. Currently has a malignancy or has a history of malignancy within 5 years before screening (with the exception of a nonmelanoma skin cancer that has been adequately treated with no evidence of recurrence for at least 3 months [defined as a minimum of 12 weeks] before the first dose of study intervention or cervical carcinoma in situ that has been treated with no evidence of recurrence for at least 3 months before the first dose of study intervention).

22. Has a known history of lymphoproliferative disease, including lymphoma, a history of monoclonal gammopathy of undetermined significance; or signs and symptoms suggestive of possible lymphoproliferative disease, such as lymphadenopathy or splenomegaly.

Coexisting Medical Conditions or Past Medical History

23. Has a history of severe, progressive, or uncontrolled renal, genitourinary, hematologic, endocrine, cardiac, vascular, pulmonary, rheumatologic, neurologic, psychiatric, or metabolic disturbances, or signs and symptoms thereof.

24. Has a transplanted organ (with exception of a corneal transplant >12 weeks before screening).

25. Poor tolerability of venipuncture or lacks adequate venous access for required blood sample collections during the study period.

26. History of drug or alcohol abuse according to Diagnostic and Statistical Manual of Disorders (5th edition) criteria within 1 year before screening.

27. Has unstable suicidal ideation or suicidal behavior in the last 6 months that may be defined as a Columbia-Suicide Severity Rating Scale (C—SSRS) rating at screening of: suicidal ideation with intention to act ("Ideation level 4"), suicidal ideation with specific plan and intent ("Ideation level 5"), or suicidal behavior (actual suicide attempt, interrupted suicide attempt, aborted suicide attempt, or preparatory behaviors for making a suicide attempt), and is considered to be at risk by the investigator based on an evaluation by a mental health professional. In addition, participants with C—SSRS ratings of wish to be dead ("Ideation level 1"), non-specific active suicidal thoughts ("Ideation level 2"), active suicidal ideation with any methods (not plan) without intent to act ("Ideation level 3") or non-suicidal self-injurious behavior who are determined to be at risk by the investigator may not be randomized.
28. Has known allergy, hypersensitivity, or intolerance to guselkumab or its excipients.
29. Is a woman who is pregnant, or breastfeeding, or planning to become pregnant while enrolled in this study or within 12 weeks after the last dose of study intervention.
30. Is a man who plans to father a child while enrolled in this study or within 12 weeks after the last dose of study intervention.

General

31. Currently participating or intends to participate in any other study using an investigational agent or procedure during the conduct of this study.
32. Has any condition for which, in the opinion of the investigator, participation would not be in the best interest of the participant (e.g., compromise the well-being) or that could prevent, limit, or confound the protocol-specified assessments.
33. Is an employee of the investigator or study site, with direct involvement in the proposed study or other studies under the direction of that investigator or study site, as well as family members of the employees or the investigator.

A study duration of 24 weeks is thought to be sufficient to evaluate efficacy and safety of SC induction followed by SC maintenance of guselkumab in Crohn's disease. The guselkumab dosing regimen after Week 8 in this study is identical to that in the ongoing guselkumab Phase 3 Crohn's studies (GALAXI 2 and 3). After Week 24, no differences in guselkumab concentrations and exposures are expected between 400 mg SC induction (in this study) and 200 mg IV induction (GALAXI) dose regimens. Consequently, this study is a 24-week study with a 72-week extension. The extension will give participants who are deemed by the investigator to be benefiting from study intervention, access to treatment for approximately 2 years. The follow-up phase (approximately 12 weeks after the last dose of study intervention) is designed to assess the final efficacy and safety data as well as to collect samples for determination of PK and antibodies to guselkumab.

Biomarker and DNA Collection

Biomarker samples (where local regulations permit) will be collected to evaluate the cellular and molecular mechanism of action of guselkumab, or help to explain interindividual variability in clinical outcomes, or may help to identify population subgroups that respond differently to an intervention. Serum biomarkers will be collected from whole blood in all participants to assess PD markers associated with the IL-23 pathway, and with response to guselkumab. Whole blood samples will be collected from all participants to assess the effect of study intervention on ribonucleic acid (RNA) expression profiles. Ileocolonic biopsies will also be obtained from all participants to assess cellular and molecular changes within the intestinal mucosal tissue. The goal of the biomarker analyses is to further define the mechanism of action of the selective blockade of IL-23 with guselkumab in Crohn's disease, and aid in evaluating the intervention-clinical response relationship.

An optional pharmacogenomic substudy is planned. It is recognized that genetic variation can be an important contributory factor to interindividual differences in intervention distribution and response and can also serve as a marker for disease susceptibility and prognosis. The goal of the pharmacogenomic component is to collect DNA to allow the identification of genetic factors that may influence the PK, PD, efficacy, safety, or tolerability of guselkumab and to identify genetic factors associated with Crohn's disease or the response to guselkumab treatment. The focus of this analysis will be the evaluation of genetic single nucleic polymorphisms associated with Crohn's disease and response to treatment with guselkumab.

Biomarker and DNA samples may be used to help address emerging issues and to enable the development of safer, more effective, and ultimately individualized therapies.

Patient-Reported Outcomes on Health-Related Quality of Life

Patient-reported outcome evaluations (i.e., IBDQ, PROMIS-29) will be used to assess the benefits of guselkumab treatment on disease-specific and general health-related quality of life (HRQOL). Patient-reported outcome evaluations are only being collected in countries where translations of the evaluations are available.

Oral Corticosteroids Tapering

Participants on corticosteroids will undergo mandatory tapering from Week 12 onwards according to pre-defined recommended tapering schedule given that obtaining corticosteroid-free clinical remission is an important goal of therapy.

Description of Interventions

Guselkumab will be provided in 2 dose strengths: guselkumab 200 mg/2 mL in a single-dose prefilled syringe with YpsoMate autoinjector (PFS-Y) and 100 mg/l mL in a single-dose prefilled syringe with an UltraSafe Plus™ Passive Needle Guard (PFS-U). Matching placebo will be provided as 2 mL in a single-dose PFS-Y and as 1 mL in a single dose PFS-U.

Efficacy Evaluations

Efficacy evaluations will include the following:

CDAI.

PRO-2 (the unweighted CDAI components of the total number of liquid or very soft stools and the abdominal pain [AP] score)

Endoscopic assessments of the intestinal mucosa based on the presence and absence of mucosal ulcerations and the SES-CD Histologic assessments Inflammatory pharmacodynamic (PD) markers, including C-reactive protein (CRP) and fecal calprotectin Fistula assessment PRO measures to assess health-related quality of life outcomes including Inflammatory Bowel Disease Questionnaire (IBDQ) and Patient-reported Outcomes Measurement Information System (PROMIS)-29

Patient-reported symptom measures including Bristol Stool Form Scale (BSFS) and AP-Numerical Rating Scale (NRS)

Pharmacokinetic Evaluations

Serum samples will be analyzed to determine concentrations of guselkumab using validated, specific, and sensitive immunoassay methods by or under the supervision of the sponsor.

Pharmacogenomic (DNA) Evaluations

A pharmacogenomic blood sample will be collected only from participants who consent separately to this component of the study to allow for pharmacogenomic research, as necessary (where local regulations permit). Participation in the pharmacogenomic research is optional. Deoxyribonucleic acid (DNA) samples will be analyzed for identification of genetic factors that may be associated with clinical response.

Pharmacodynamic and Biomarker Evaluations

Inflammatory PD markers (CRP and fecal calprotectin) will be evaluated using blood and fecal samples. Biomarker assessments will be made to examine the biologic response to treatment and to identify biomarkers that are relevant to guselkumab treatment and/or Crohn's disease. Assessments will include the evaluation of relevant biomarkers in serum, whole blood, and ileocolonic biopsy samples, where local regulations permit.

Immunogenicity Evaluations

Serum samples will be screened for antibodies binding to guselkumab and the titer of confirmed positive samples will be reported. Other analyses may be performed to verify the stability of antibodies to guselkumab and/or further characterize the immunogenicity of guselkumab.

Safety Evaluations

Safety assessments include adverse events (AEs), clinical laboratory tests, vital signs and physical examinations, a screening electrocardiogram, suicidality assessment, concomitant medication review, injection-site reactions, monitoring for hypersensitivity reactions, a tuberculosis evaluation and other infection assessment.

Statistical Methods

Sample Size Determination

Sample sizes were determined by the power to detect a significant difference in clinical remission at Week 12 and in endoscopic response at Week 12 (co-primary endpoints) between the combined guselkumab group and the placebo group, using a 2-sided chi-square test with 0.05 significance level. The assumed rates are 50% versus 15% (guselkumab versus placebo) for clinical remission and 30% versus 13% for endoscopic response. The study is sized such that the guselkumab therapy achieves >90% power for the co-primary endpoints compared with placebo. This sample size also provides >90% power for all secondary endpoints.

Efficacy Analyses

Descriptive statistics (e.g., mean, median, standard deviation [SD], interquartile range, minimum, and maximum) will be used to summarize continuous variables. Counts and percentages will be used to summarize categorical variables. Graphical data displays (e.g., line plots) may also be used to summarize data.

Analyses suitable for categorical data (e.g., chi-square tests, Cochran-Mantel-Haenszel (CMH) chi-square tests, or logistic regression, as appropriate) will be used to compare the proportions of participants achieving selected endpoints (e.g., clinical response). In cases of rare events, the Fisher's exact test will be used for treatment comparisons. Continuous response parameters will be compared using an analysis of variance (ANOVA) or analysis of covariance (ANCOVA), unless otherwise specified. If the normality assumption is in question, an ANOVA or ANCOVA on the van der Waerden normal scores will be used.

The co-primary endpoints (clinical remission at Week 12 and endoscopic response at Week 12) will be analyzed based on the primary estimates and, considering treatment groups, population, variable, intercurrent event (ICE) strategies, and population-level summary. After accounting for the ICE strategies, participants whose responder status is missing for a co-primary endpoint will be considered to be a non-responder for that co-primary endpoint.

Statistical testing will be performed at a significance level of 0.05 (2-sided). The Type I error will be controlled over the co-primary and secondary endpoints. For the co-primary endpoints, clinical remission at Week 12 will be tested first, followed by endoscopic response at Week 12. The 3 secondary analyses listed below will be performed sequentially contingent upon the success of both co-primary endpoint analyses.

- Clinical remission (CDAI score <150) at Week 24.
- PRO-2 remission at Week 12 (defined as an AP mean daily score at or below 1 and stool frequency (SF) mean daily score at or below 3, i.e., AP≤1 and SF≤3, and no worsening of AP or SF from baseline)
- Clinical response (decrease from baseline in CDAI ≥100 points or clinical remission) at Week 12

For endpoints that are not multiplicity-controlled, nominal p-values will be presented.

Safety Analyses

Safety data, including but not limited to, AEs, serious adverse events (SAEs), infections, injection-site reactions, changes in laboratory parameters (hematology and chemistry), and suicidal ideation and behavior will be summarized. All reported treatment-emergent AEs will be included in the analysis.

Other Analyses

Pharmacokinetic Analyses

Serum guselkumab concentration over time will be summarized for each treatment group using descriptive statistics. Population PK modeling may be conducted when appropriate. If these population PK analyses are conducted, the results of these analyses will be presented in a separate report.

Pharmacokinetic/Pharmacodynamic Analyses

The relationship between serum guselkumab concentrations and efficacy measures will be analyzed graphically. If feasible, a suitable exposure-response model may be developed to describe the relationship between serum guselkumab exposure and efficacy. Results of the population PK/PD analysis will be presented in a separate technical report.

Pharmacogenomic Analyses

Genetic (DNA) analyses will be conducted only in participants who sign the consent form to participate in the pharmacogenomic substudy. These analyses are considered exploratory and will be summarized in a separate technical report.

Biomarker Analyses

Changes in serum protein analytes and whole blood ribonucleic acid (RNA) obtained over time will be summarized by intervention group where local regulations permit. Associations between baseline levels and changes from baseline in select biomarkers and response to treatment will be explored. RNA analyses will be summarized in a separate technical report.

Immunogenicity Analyses

The incidence and titers of antibodies to guselkumab will be summarized for all participants who receive a dose of guselkumab and have appropriate samples for detection of antibodies to guselkumab (i.e., participants with at least 1 sample obtained after their first dose of guselkumab). The incidence of neutralizing antibodies to guselkumab will be summarized for participants who are positive for antibodies to guselkumab and have samples evaluable for neutralizing antibodies to guselkumab.

What is claimed:

1. A method of treating Crohn's disease in a patient, comprising administering to the patient an initial subcutaneous induction dose of 400 mg of an antibody specific to IL23, a 400 mg subcutaneous dose about 4 weeks after the initial subcutaneous induction dose, and a 400 mg subcutaneous dose about 8 weeks after the initial subcutaneous induction dose, wherein the antibody comprises a light chain variable region and a heavy chain variable region, said light chain variable region comprising:

- a complementarity determining region light chain 1 (CDRL1) amino acid sequence of SEQ ID NO:4;
- a CDRL2 amino acid sequence of SEQ ID NO:5; and
- a CDRL3 amino acid sequence of SEQ ID NO:6, said heavy chain variable region comprising:

- a complementarity determining region heavy chain 1 (CDRH1) amino acid sequence of SEQ ID NO:1;
- a CDRH2 amino acid sequence of SEQ ID NO:2; and
- a CDRH3 amino acid sequence of SEQ ID NO:3.

2. The method of claim 1, further comprising administering a dose of 100 mg or 200 mg of the antibody about every 4 weeks or about every 8 weeks after the subcutaneous dose at about 8 weeks after the subcutaneous induction dose.

3. The method of claim 2, further comprising administering a dose of 200 mg of the antibody about every 4 weeks after the subcuteanous dose at about 8 weeks after the initial subcutaneous induction dose.

4. The method of claim 2, further comprising administering a dose of 100 mg of the antibody about every 8 weeks after the subcutaneous dose at about 8 weeks after the initial subcutaneous induction dose.

5. The method of claim 1, wherein the patient is a responder to the antibody and is identified as meeting a clinical endpoint about 12 weeks after the initial subcuteanous induction dose, wherein the clinical endpoint is clinical remission at Week 12, defined as CDAI less than (<) 150 points or endoscopic response measured by at least a 50% improvement from baseline in the Simple Endoscopic Score for Crohn's Disease (SES-CD).

6. The method of claim 1, wherein the patient is identified as meeting a clinical endpoint, wherein the clinical endpoint is selected from the group consisting of: (i) clinical remission, defined as CDAI less than (<) 150 points measured at about 24 weeks after the initial subcuteanous induction dose; (ii) Patient-Reported Outcome (PRO)-2 remission defined based on average daily stool frequency (SF)≤3 and average daily abdominal pain (AP) score≤1 and no worsening of AP or SF from baseline measured at about 12 weeks after the initial subcutaneous induction dose; and (iii) clinical response, defined as greater than or equal to (≥) 100-point reduction from baseline in CDAI score measured at about 12 weeks after the initial subcutaneous induction dose.

7. The method of claim 1, wherein the patient is deemed a responder to the antibody.

8. The method of claim 7, wherein the patient is a responder to the antibody and is identified as meeting a clinical endpoint selected from one of:

- (i) Change from Baseline in the Crohn's Disease Activity Index (CDAI) Score;
- (ii) Clinical remission, defined as CDAI less than (<) 150 points;
- (iii) Clinical response, defined as greater than or equal to (>=) 100-point reduction from baseline in CDAI score or CDAI score <150;
- (iv) Patient-Reported Outcome (PRO)-2 Remission, defined based on average daily stool frequency (SF) and average daily abdominal pain (AP) score;
- (v) Clinical-Biomarker Response, defined using clinical response based on the CDAI score and reduction from baseline in C-reactive protein (CRP) or fecal calprotectin;
- (vi) Endoscopic Response, measured by the Simple Endoscopic Score for Crohn's Disease (SES-CD):
- (vii) Endoscopic Remission, measured by the Simple Endoscopic Score for Crohn's Disease (SES-CD);
- (viii) Durable Clinical Remission at Week 48, defined as CDAI<150 for most of all visits between Week 12 and Week 48;
- (ix) Corticosteroid-Free Clinical Remission at Week 48, defined as CDAI score <150 at Week 48 and not receiving corticosteroids at Week 48; and
- (x) Fatigue response based on the Patient-Reported Outcomes Measurement Information System (PROMIS).

9. The method of claim 8, wherein the clinical endpoint(s) is measured 4, 8, 12, 16, 20, 28, 32, 36, 40, 44 and/or 48 weeks after initial treatment.

10. The method of claim 7, wherein the antibody is in a pharmaceutical composition comprising sucrose, Histidine, L-Histidine monohydrochloride monohydrate, Polysorbate 80, and a diluent comprising water at standard state.

11. The method of claim 1, further comprising administering to the patient one or more additional drugs used to treat Crohn's disease.

12. The method of claim 11, wherein the additional drug is selected from the group consisting of: immunosuppressive agents, non-steroidal anti-inflammatory drugs (NSAIDs), methotrexate (MTX), anti-B-cell surface marker antibodies, anti-CD20 antibodies, rituximab, TNF-inhibitors, corticosteroids, and co-stimulatory modifiers.

13. The method of claim 1, wherein the antibody comprises a light chain variable region amino acid sequence of SEQ ID NO: 8 and a heavy chain variable region amino acid sequence of SEQ ID NO: 7.

14. The method of claim 1, wherein the antibody comprises a light chain amino acid sequence of SEQ ID NO: 10 and a heavy chain amino acid sequence of SEQ ID NO: 9.

15. The method of claim 1, wherein the patient is considered a biologic therapy failure or intolerance for Crohn's disease (Bio-Failure).

16. The method of claim 1, wherein the patient is considered a conventional therapy failure or intolerance for Crohn's disease (Con-Failure).

17. The method of claim 1, wherein the Crohn's disease is moderately to severely active Crohn's disease.

18. The method of claim 17, wherein the patient has endoscopic evidence of active Crohn's disease prior to administration of the initial subcutaneous induction dose.

19. The method of claim 17, wherein the patient has moderately to severely active Crohn's disease for at least three months prior to administration of the initial subcutaenou induction dose.

20. A method of treating moderately to severely active Crohn's disease in a patient, comprising (i) administering to the patient an initial subcutaneous induction dose of 400 mg of an antibody specific to IL23, a 400 mg subcutaneous dose about 4 weeks after the initial subcutaneous induction dose and a 400 mg subcutaneous dose about 8 weeks after the initial subcutaneous induction dose, and (ii) further administering a dose of 200 mg of antibody about every 4 weeks after the subcutaneous dose at about 8 weeks after the initial subcutaneous induction dose or a dose of 100 mg of antibody about every 8 weeks after the subcutaneous dose at about 8 weeks after the initial subcutaneous induction dose, wherein the antibody comprises a light chain variable region amino acid sequence of SEQ ID NO: 8 and a heavy chain variable region amino acid sequence of SEQ ID NO: 7, and the patient is a responder to the antibody by being identified as meeting a clinical endpoint about 12 weeks after the initial subcutaneous dose, wherein the clinical endpoint is clinical remission at Week 12, defined as CDAI less than (<) 150 points or endoscopic response measured by at least a 50% improvement from baseline in the Simple Endoscopic Score for Crohn's Disease (SES-CD).

21. A method of treating Crohn's disease in a patient, comprising administering to the patient an initial subcutaneous induction dose of 400 mg of an antibody specific to IL23, a 400 mg subcutaneous dose about 4 weeks after the initial subcutaneous induction dose, and a 400 mg subcutaneous dose about 8 weeks after the initial subcutaneous induction dose, wherein the initial subcutaneous induction dose of 400 mg, the 400 mg subcutaneous dose about 4 weeks after the initial subcutaneous induction dose, and the 400 mg subcutaneous dose about 8 weeks after the initial subcutaneous induction dose are administered in two consecutive 2 mL injections, wherein each of the 2 mL injections comprises a 200 mg dose, wherein the antibody comprises a light chain variable region amino acid sequence of SEQ ID NO: 8 and a heavy chain variable region amino acid sequence of SEQ ID NO: 7.

22. The method of claim 21, further comprising administering a dose of 100 mg or 200 mg of the antibody about every 4 weeks or about every 8 weeks after the subcutaneous dose at about 8 weeks after the initial subcutaneous induction dose.

23. The method of claim 22, further comprising administering a dose of 200 mg of the antibody about every 4 weeks after the subcutaneous dose at about 8weeks after the initial subcutaneous induction dose.

24. The method of claim 22, further comprising administering a dose of 100 mg of the antibody about every 8 weeks after the subcutaneous dose at about 8weeks after the initial subcutaneous induction dose.

25. The method of claim 21, wherein the patient is a responder to the antibody and is identified as meeting a clinical endpoint about 12 weeks after the initial subcutaneous induction dose, wherein the clinical endpoint is clinical remission at Week 12,defined as CDAI less than (<) 150 points or endoscopic response measured by at least a 50% improvement from baseline in the Simple Endoscopic Score for Crohn's Disease (SES-CD).

26. The method of claim 21, wherein the patient is considered a conventional therapy failure or intolerance for Crohn's disease (Con-Failure).

27. The method of claim 21, wherein the Crohn's disease is moderately to severely active Crohn's disease.

28. The method of claim 27, wherein the patient has endoscopic evidence of active Crohn's disease prior to administration of the initial subcutaneous induction dose.

29. The method of claim 27, wherein the patient has moderately to severely active Crohn's disease for at least three months prior to administration of the initial subcutaneous induction dose.

* * * * *

SEQUENCE LISTING

```
Sequence total quantity: 10
SEQ ID NO: 1            moltype = AA  length = 5
FEATURE                 Location/Qualifiers
source                  1..5
                        mol_type = protein
                        organism = Homo sapiens
SEQUENCE: 1
NYWIG                                                                5

SEQ ID NO: 2            moltype = AA  length = 17
FEATURE                 Location/Qualifiers
source                  1..17
                        mol_type = protein
                        organism = Homo sapiens
SEQUENCE: 2
IIDPSNSYTR YSPSFQG                                                   17

SEQ ID NO: 3            moltype = AA  length = 8
FEATURE                 Location/Qualifiers
source                  1..8
                        mol_type = protein
                        organism = Homo sapiens
SEQUENCE: 3
WYYKPFDV                                                             8

SEQ ID NO: 4            moltype = AA  length = 14
FEATURE                 Location/Qualifiers
source                  1..14
                        mol_type = protein
                        organism = Homo sapiens
SEQUENCE: 4
TGSSSNIGSG YDVH                                                      14

SEQ ID NO: 5            moltype = AA  length = 7
FEATURE                 Location/Qualifiers
source                  1..7
                        mol_type = protein
                        organism = Homo sapiens
SEQUENCE: 5
GNSKRPS                                                              7

SEQ ID NO: 6            moltype = AA  length = 11
FEATURE                 Location/Qualifiers
source                  1..11
                        mol_type = protein
                        organism = Homo sapiens
SEQUENCE: 6
ASWTDGLSLV V                                                         11

SEQ ID NO: 7            moltype = AA  length = 117
FEATURE                 Location/Qualifiers
source                  1..117
                        mol_type = protein
                        organism = Homo sapiens
SEQUENCE: 7
EVQLVQSGAE VKKPGESLKI SCKGSGYSFS NYWIGWVRQM PGKGLEWMGI IDPSNSYTRY  60
SPSFQGQVTI SADKSISTAY LQWSSLKASD TAMYYCARWY YKPFDVWGQG TLVTVSS     117

SEQ ID NO: 8            moltype = AA  length = 111
FEATURE                 Location/Qualifiers
source                  1..111
                        mol_type = protein
                        organism = Homo sapiens
SEQUENCE: 8
QSVLTQPPSV SGAPGQRVTI SCTGSSSNIG SGYDVHWYQQ LPGTAPKLLI YGNSKRPSGV  60
PDRFSGSKSG TSASLAITGL QSEDEADYYC ASWTDGLSLV VFGGGTKLTV L           111

SEQ ID NO: 9            moltype = AA  length = 447
FEATURE                 Location/Qualifiers
source                  1..447
                        mol_type = protein
                        organism = Homo sapiens
```

-continued

```
SEQUENCE: 9
EVQLVQSGAE VKKPGESLKI SCKGSGYSFS NYWIGWVRQM PGKGLEWMGI IDPSNSYTRY  60
SPSFQGQVTI SADKSISTAY LQWSSLKASD TAMYYCARWY YKPFDVWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 10          moltype = AA  length = 217
FEATURE                Location/Qualifiers
source                 1..217
                       mol_type = protein
                       organism = Homo sapiens
SEQUENCE: 10
QSVLTQPPSV SGAPGQRVTI SCTGSSSNIG SGYDVHWYQQ LPGTAPKLLI YGNSKRPSGV  60
PDRFSGSKSG TSASLAITGL QSEDEADYYC ASWTDGLSLV VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                          217
```